United States Patent
Koch et al.

(10) Patent No.: US 7,018,992 B2
(45) Date of Patent: Mar. 28, 2006

(54) HORMONE COMPOSITION

(75) Inventors: Karen Koch, Charlottenlund (DK); Ingelise Kvorning, Bronshoj (DK)

(73) Assignee: Novo Nordisk A/S, Bagsvaerd (DK)

( * ) Notice: Subject to any disclaimer, the term of this patent is extended or adjusted under 35 U.S.C. 154(b) by 277 days.

(21) Appl. No.: 10/016,858

(22) Filed: Dec. 14, 2001

(65) Prior Publication Data

US 2003/0064975 A1 Apr. 3, 2003

Related U.S. Application Data

(60) Provisional application No. 60/260,182, filed on Jan. 5, 2001, provisional application No. 60/260,183, filed on Jan. 5, 2001, and provisional application No. 60/260,184, filed on Jan. 5, 2001.

(30) Foreign Application Priority Data

Dec. 15, 2000 (DK) ........................................ 2000 01891
Dec. 15, 2000 (DK) ........................................ 2000 01892
Dec. 15, 2000 (DK) ........................................ 2000 01890

(51) Int. Cl.
*A61K 31/56* (2006.01)

(52) U.S. Cl. .................................................... 514/178
(58) Field of Classification Search ................. 514/178
See application file for complete search history.

(56) References Cited

U.S. PATENT DOCUMENTS 6,060,077 A * 5/2000 Meignant

FOREIGN PATENT DOCUMENTS

WO WO 97/12600 4/1997

OTHER PUBLICATIONS

Smith et al., Maturitas, 1993;16(2):145–154.*
Vagifem monograph, Novo Nordisk, Jun. 2000.*
McCane, "Pathophysilogy: the biologic basis for disease in adults and children", published by Mosby, 1990, p. 989.*
Mettler et al., Maturitas, vol. 14, pp. 23–31 (1991).
Kvorning et al., Saidioc and Eriksen, Editors, The Urogenital Oestrogen Deficiency Syndrome, Proceedings of the International Workshop, Copenhagen, pp. 51–60 (1986).
Nilssom et al., Mamriras, vol. 15, pp. 121–127 (1992).
Dugal et al., Acta Obstet. Gynecol. Scan., vol. 79, pp. 293–297 (2000).

* cited by examiner

*Primary Examiner*—San-Ming Hui
(74) *Attorney, Agent, or Firm*—Reza Green; Len S. Smith; Richard Bork

(57) ABSTRACT

Twice weekly administration of an analog to a Vagifem tablet which only contains 10 μg of active material has a sufficient effect.

12 Claims, 18 Drawing Sheets

Figure 11:
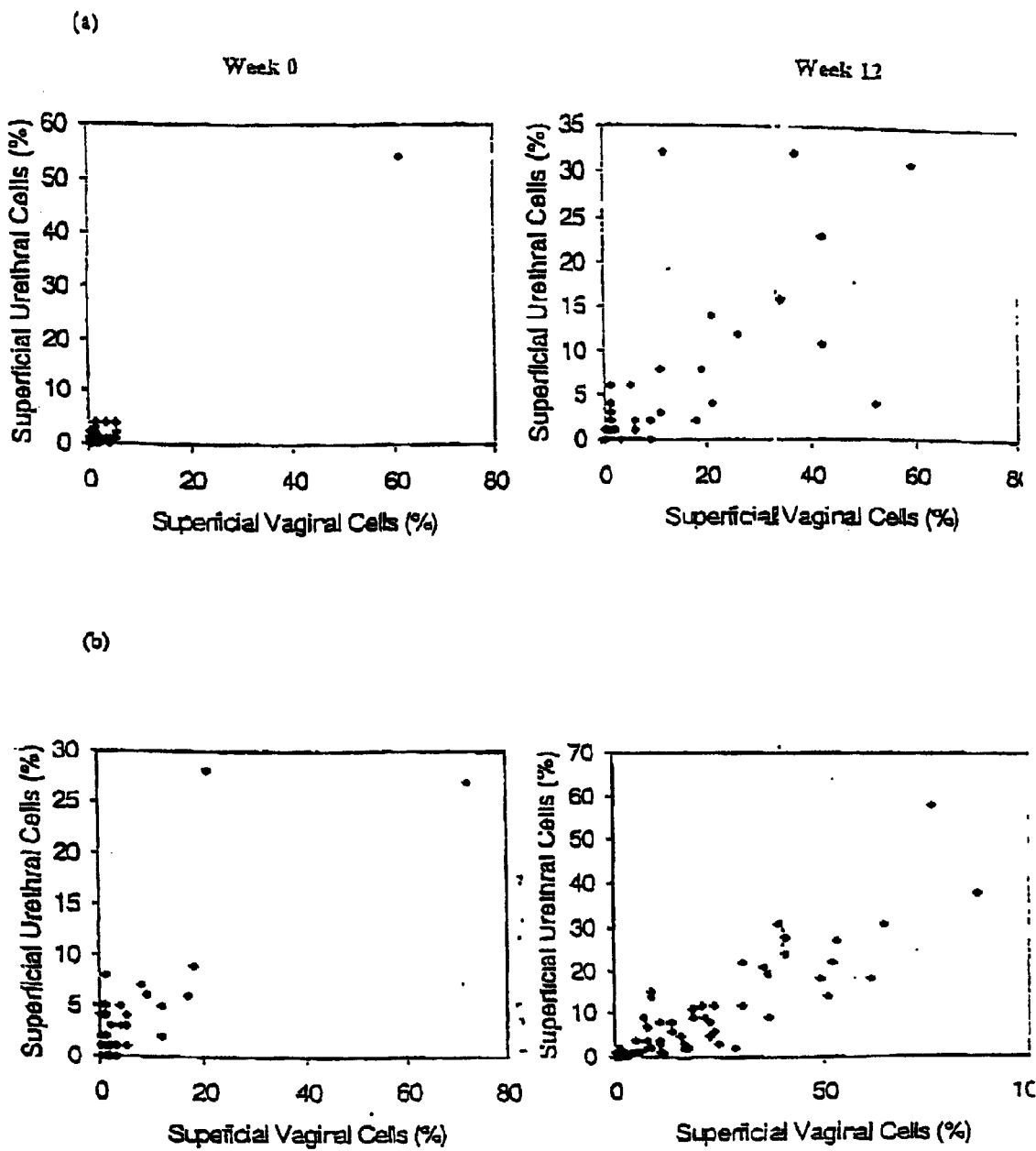

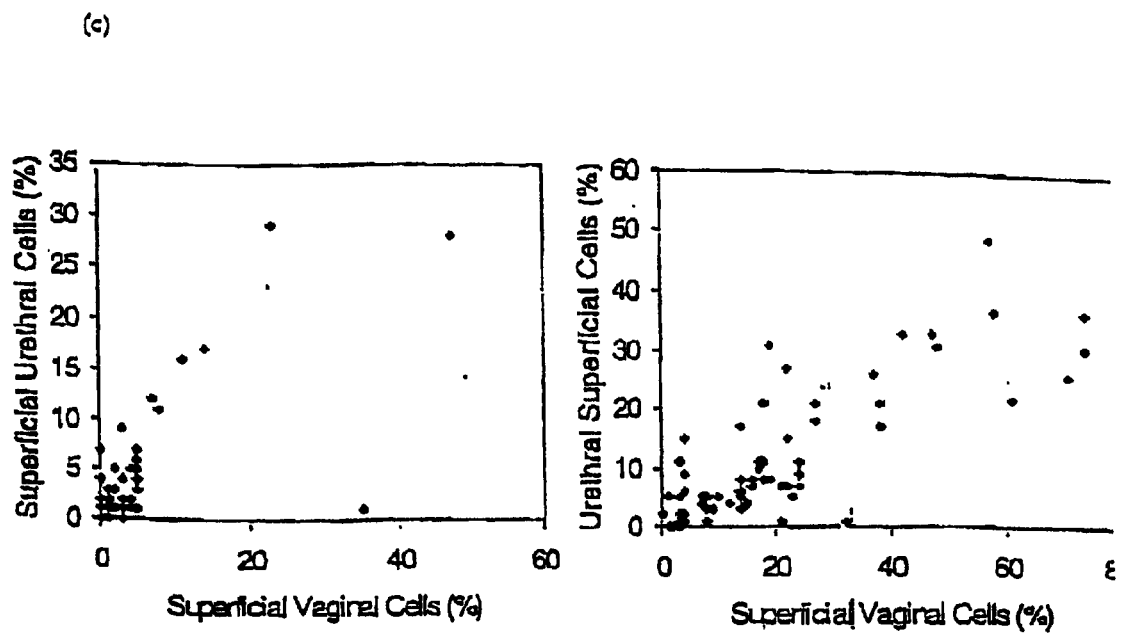
FIG. 11 - continued

Fig. 12 (a)
Week 0
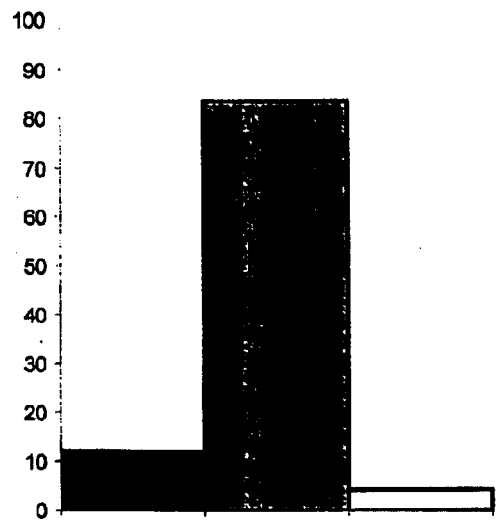
Week 2
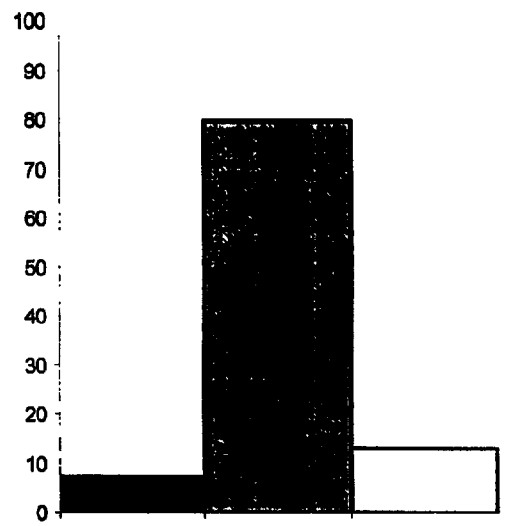
Week 7
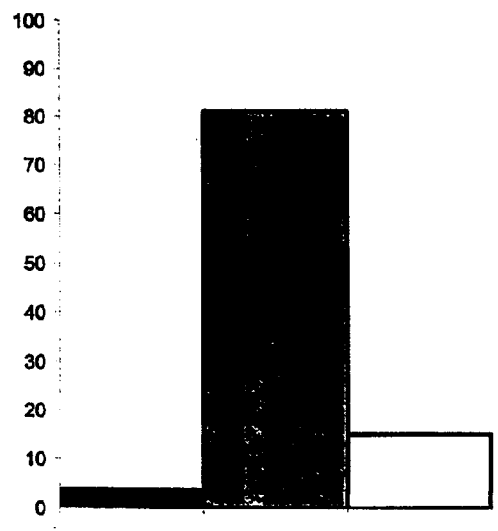
Week 12
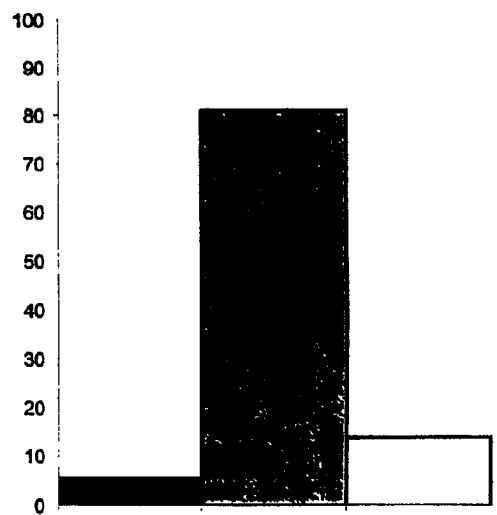

Fig. 12 (b)
Week 0
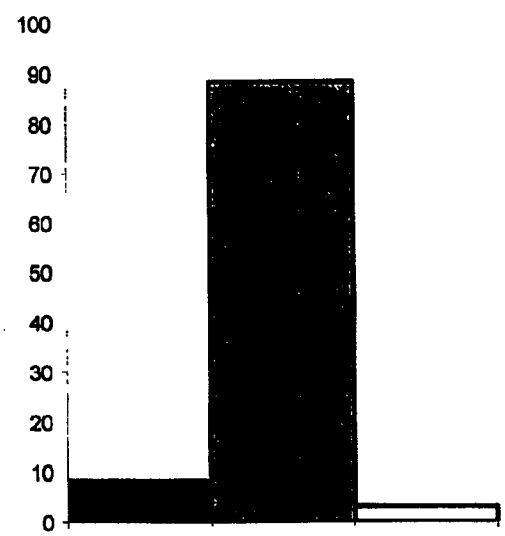
Week 2
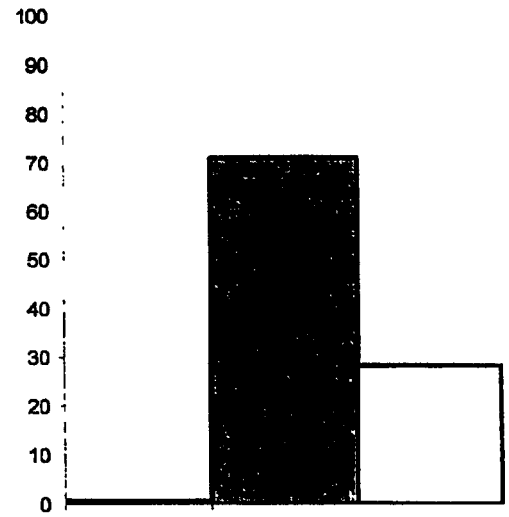
Week 7
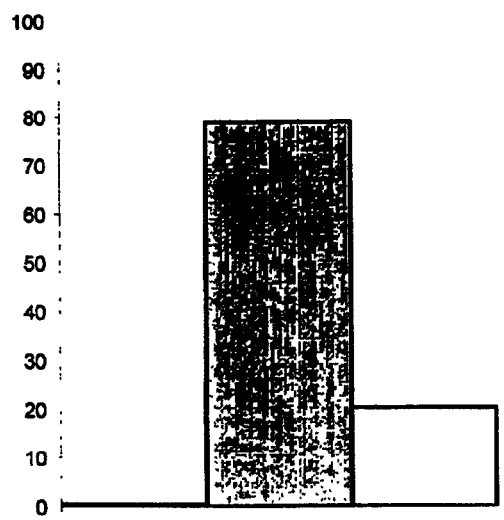
Week 12
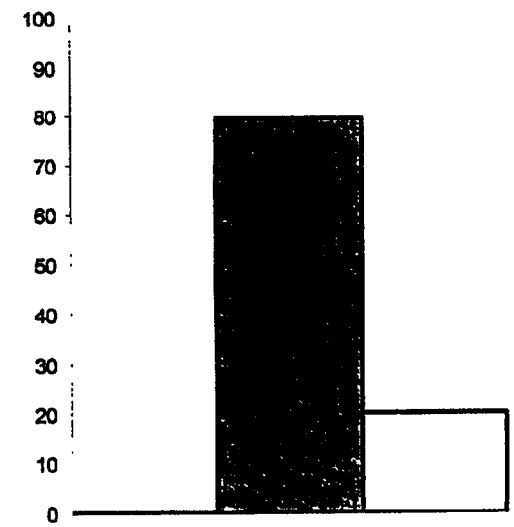

Fig. 12 (c)
Week 0
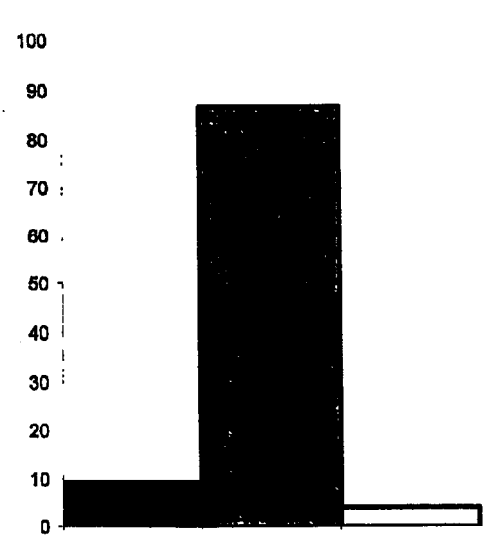
Week 2
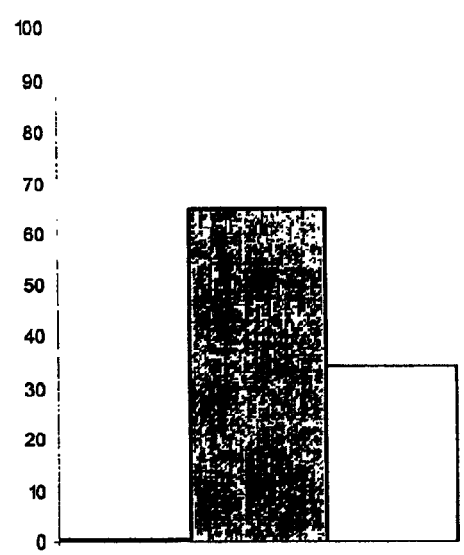
Week 7
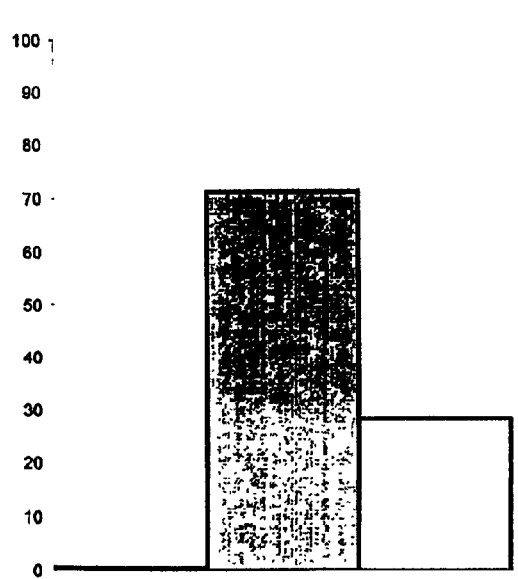
Week 12
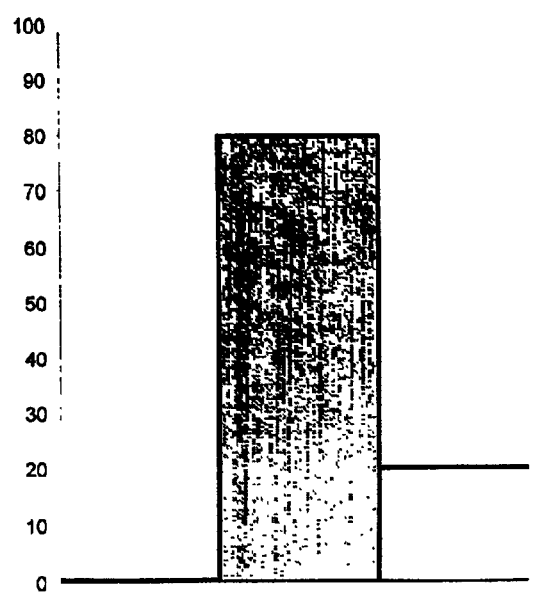

Figure 13:
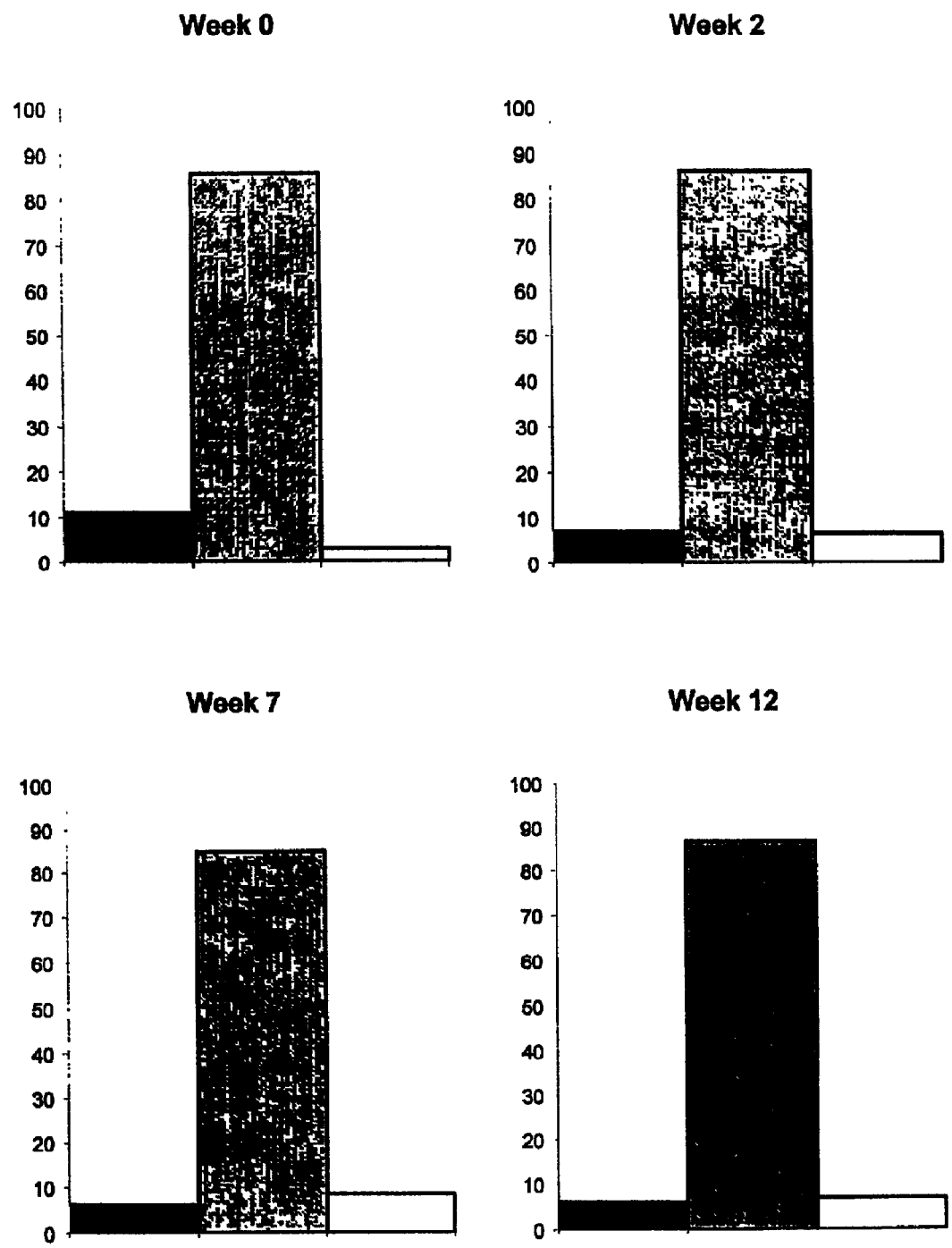

Fig. 13 (b)
Week 0
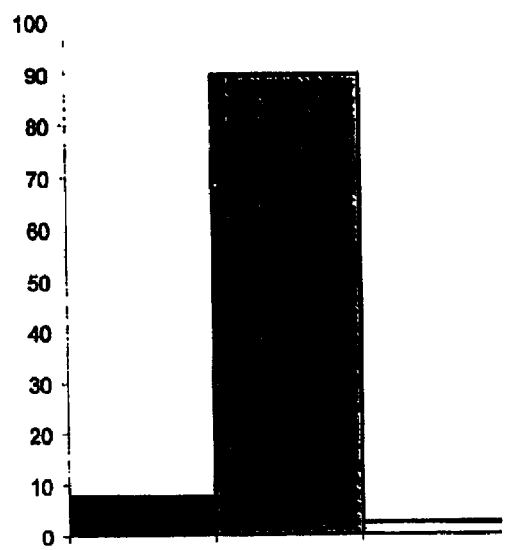
Week 2
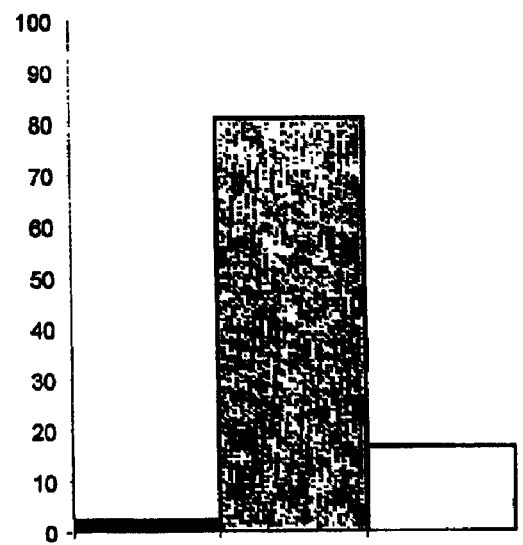
Week 7
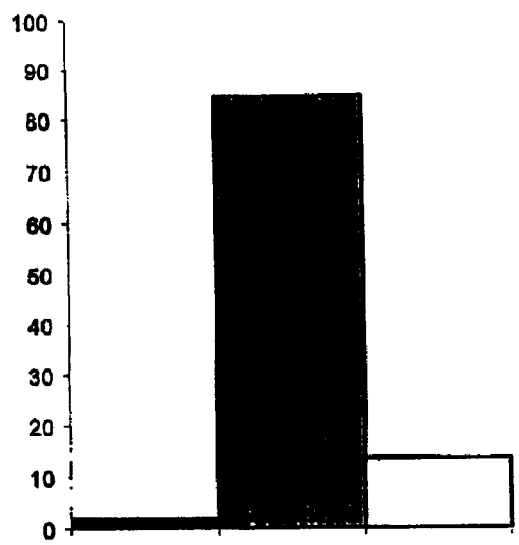
Week 12
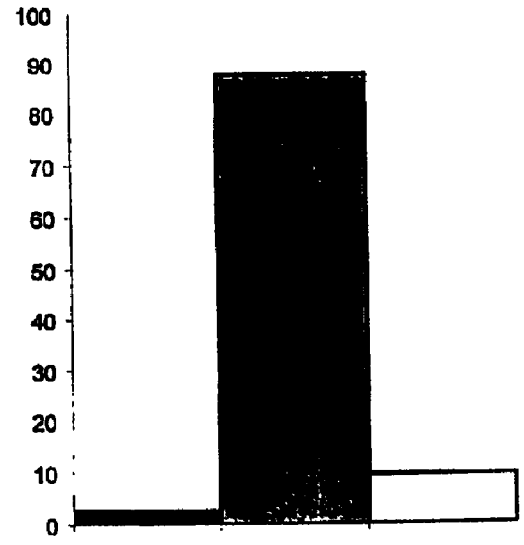

Fig. 13 (c)
Week 0
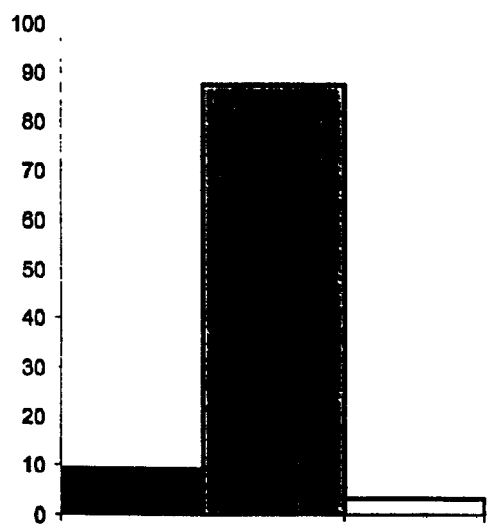
Week 2
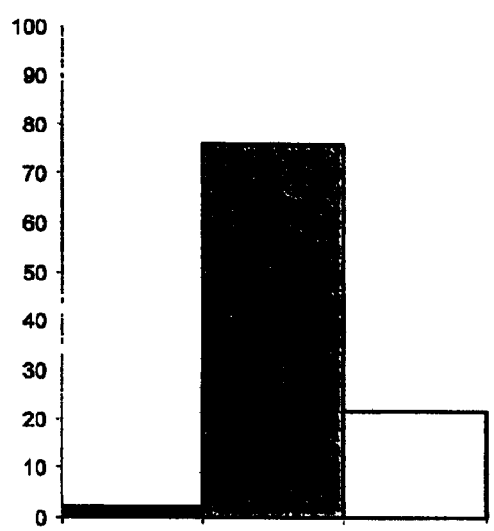
Week 7
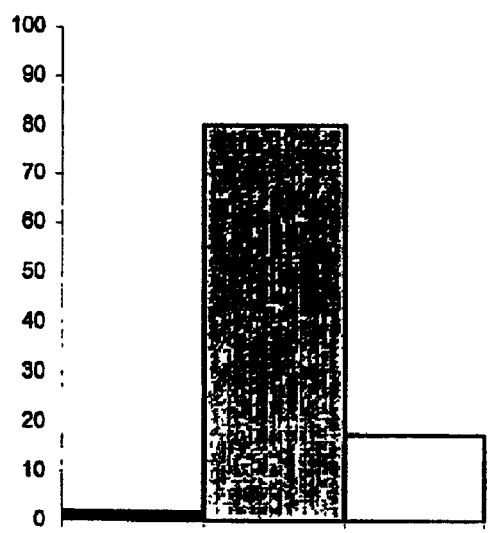
Week 12
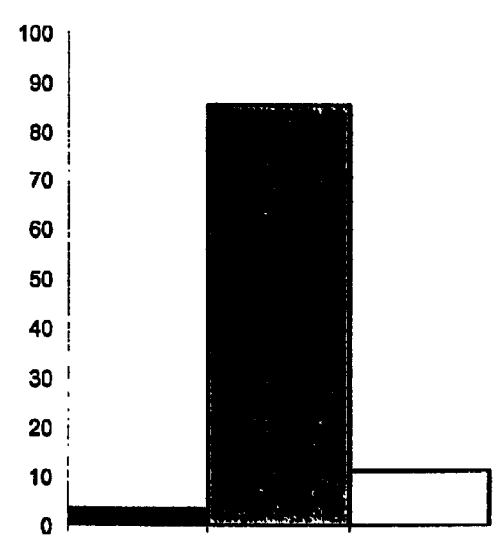

HORMONE COMPOSITION

CROSS-REFERENCE TO RELATED APPLICATIONS

This application claims priority under 35 U.S.C. 119 of Danish application PA 2000 01890 filed on Dec. 15, 2000; PA 2000 01891 filed on Dec. 15, 2000; and PA 2000 01892 filed on Dec. 15, 2000; and of U.S. application Nos. 60/260,182 filed Jan. 5, 2001, 60/260,183 filed on Jan. 5, 2001 and 60/260,184 filed on Jan. 5, 2001, the contents of which are fully incorporated herein by reference.

The present invention relates to a composition containing oestrogen, which is to be administered vaginally.

BACKGROUND OF THIS INVENTION

Vaginal atrophy can occur in postmenopausal woman and estrogen deprived women who actually do not need any systemic hormone replacement therapy but just local therapy. Consequently, local, topical treatment is preferred in order to avoid the systemic side effects due to long-lasting oestrogen therapy. Local therapy for this purpose has been studied for a long period of time and the hormone has been administered as creams, gels, and silastic rings.

About every second postmenopausal women will experience urogenital discomfort associated with estrogen deficiency. Previous studies have shown that although many of these women use an oral hormone replacement therapy, urogenital symptoms persist.

A composition commonly used is Vagifem® marketed by Novo Nordisk A/S. Vagifem is developed to treat estrogen deficiency-deprived atrophic vaginitis. Vagifem is a small tablet containing 25 μg 17β-estradiol. For example, reference can be made to Maturitas 14 (1991), 23–31, where the women initially received 25 μg estradiol for 2 weeks and, thereafter, 25 μg estradiol once weekly or twice weekly. A usual treatment is one tablet of Vagifem containing 25 μg estradiol daily for the first 2 weeks of treatment and, thereafter, one tablet twice a week.

Conveniently, Vagifem is administered by placing a tablet at the top of a slim-line pencil-like disposable applicator. By introducing the applicator to the vagina, the Vagifem tablet will, due to the adhesive characteristics of Vagifem, stay in the vagina.

A pharmaceutical medicament for local, essentially non-systemic, treatment of vaginal dryness, in particular in the menopausal woman, characterized by a unit galenical formulation comprising a natural estrogen selected from the group consisting of 17β-estradiol and its salts and its derivatives in solution or in suspension in a lipophilic agent, with an estrogen content which corresponds to an equivalent unit dose of at most 15 μg, preferably less than 10 μg, of 17β-estradiol, a hydrophilic gel-forming bioadhesive agent, a gelling agent for the lipophilic agent, and a hydrodispersible agent, is described in U.S. Pat. No. 6,060,077. Hence, according to the U.S. Pat. No. 6,060,077 specification, 17β-estradiol and its salts and its derivatives are in solution or in suspension. Consequently, it cannot be a tablet.

SUMMARY OF THIS INVENTION

One object of this invention is to furnish a hormone composition which gives a clinical effect on vaginal symptoms which is as good as that obtained by administration of Vagifem twice weekly.

A further object of this invention is to furnish a hormone composition furnishing no or only inferior systemic absorption.

A still further object of this invention is to furnish a hormone composition furnishing significant improvement in the vaginal mucosa.

A still further object of this invention is to furnish a hormone composition furnishing no or only inferior systemic effect.

A still further object of this invention is to furnish a hormone composition furnishing low absorption of estrogen.

A still further object of this invention is to furnish a hormone composition furnishing low serum concentration of estradiol.

A still further object of this invention is to furnish a hormone composition furnishing no or only inferior accumulation of circulating estradiol.

A still further object of this invention is to furnish a hormone composition furnishing positive effects on an atrophic vaginal epithelum.

A still further object of this invention is to furnish a hormone composition furnishing complete or substantial vaginal maturation.

A still further object of this invention is to furnish a hormone composition furnishing a reduced risk of osteoporosis.

A still further object of this invention is to furnish a hormone composition furnishing increases in percentage of superficial vaginal cells.

A still further object of this invention is to furnish a hormone composition which can be used for the treatment of atrophic vaginitis.

A still further object of this invention is to furnish a hormone composition furnishing a vaginal pH value below about 5.5.

A very specific object of this invention is to furnish a hormone composition furnishing all or most of the following characteristics: Relief of vaginal symptoms, improved urogenital atrophy, decreased vaginal pH, and improved cytologic maturation of both the vaginal and urethral mucosa.

DETAILED DESCRIPTION OF THIS INVENTION

The vaginal symptoms treated by the use according to the present invention are dryness, soreness, irritation, and dyspareunia. The urogenital health is characterized by secretions, epithelial integrity, surface thickness, and the pH value of the vagina.

Surprisingly, it has been found that the use according to the claims below have pharmaceutical and clinical advantages compared with the known uses of similar compositions.

It is often recommended to precede the use according to the claims below with a treatment with a somewhat higher dosage of an estrogen, for example, estradiol. Such a treatment is herein designated a pre-treatment. In a preferred embodiment, this pre-treatment is the daily treatment with the same dose as that used for a bi-weekly use according to the claims below.

The present invention relates to use of an oestrogen in the manufacture of a composition containing oestrogen for the treatment of atrophic vaginitis in woman, by administering weekly an amount of about 10 to about 30 μg estradiol to a woman. According to a preferred embodiment, this invention relates to the use wherein the women treated is menopausal or post-menopausal women. According to a further preferred embodiment, this invention relates to the use wherein weekly an amount of about 15 to about 25 µg estradiol is administered. According to a further preferred embodiment, this invention relates to the use wherein daily about 1.5 to about 4 µg estradiol is administered. According to a further preferred embodiment, this invention relates to the use wherein daily about 2 to about 3 µg estradiol is administered. According to a further preferred embodiment, this invention relates to the use wherein twice weekly about 5 to about 15 µg estradiol is administered. According to a further preferred embodiment, this invention relates to the use wherein twice weekly about 7 to about 13 µg estradiol is administered. According to a further preferred embodiment, this invention relates to the use wherein twice weekly about 9 to about 11 µg estradiol is administered. According to a further preferred embodiment, this invention relates to the use wherein no progestogen is administered. According to a further preferred embodiment, this invention relates to the use wherein the composition is to be administered vaginally. According to a further preferred embodiment, this invention relates to the use wherein it is used for a period of time of more than 2 weeks, preferably more than 1 month, more preferred more than 2 months, and even more preferred more than 3 months. According to a further preferred embodiment, this invention relates to the use wherein administration is performed using a tablet. Furthermore, the present invention relates to a method of treating atrophic vaginitis, comprising administering a composition as described in any of the previous use claims.

The compositions used according to this invention may be prepared analogously to the preparation of similar compositions, for example, Vagifem. The compositions used according to this invention may contain any constituent used or suggest to be used in similar compositions. The compositions used according to this invention may be administered analogously with the administration of similar compositions. All these aspects are known to the skilled art worker.

According to a preferred embodiment of this invention, the composition dealt with herein is a tablet. According to a preferred embodiment, the composition dealt with herein consists of about 60% through about 80% hypromellose (or another convenient matrix former), about 20% through about 25% lactose (or another convenient filler), about 5% through about 15% maize starch (or another convenient filler), about 0.2% through about 1.5% magnesium stearate (or another convenient lubricant) and about 0.2% through about 5% film-coating, as well as E2. In a more preferred embodiment, the composition consists of about 65% through about 70% hypromellose (or another convenient matrix former), about 20% through about 24% lactose (or another convenient filler), about 8% through about 12% maize starch (or another convenient filler), about 0.3% through about 1.3% magnesium stearate (or another convenient lubricant) and about 0.3% through about 3% film-coating, as well as E2. In an even more preferred embodiment, the composition consists of about 67% hypromellose, about 22% lactose, about 10% maize starch, about 0.5% magnesium stearate and about 1% film-coating. According to a preferred embodiment of this invention, each tablet contains, in addition to the active material, about 53.7 mg hypromellose, about 17.9 mg lactose monohydrate, about 8 mg maize starch, about 0.4 mg magnesium stearate and the film-coating consisting of about 0.5 mg hypromellose and about 0.06 mg macrogel 6000 (polyethylene glycol 6000 NF).

On a dry basis. In the final tablets, the content of water is preferably below 10%, more preferred below 7%. All percentages ratios given here are per weight basis.

One way of preparing the tablets is via the following steps: Suspension of estradiol, granulation, blending, compression, preparation of film-coating solution, and film-coating.

The present invention is further illustrated by the following examples which, however, are not to be construed as limiting the scope of protection. The features disclosed in the foregoing description and in the following examples may, in any combination thereof, be material for realizing the invention in diverse forms thereof. Especially, interesting and surprising effects are dealt with and described in examples 2 & 3.

EXAMPLE 1

58 postmenopausal women were treated with tablets containing either 10 or 25 µg 17β-estradiol. The women inserted 1 tablet intravaginally, once daily for the initial 2 weeks of the study and then twice per week (Sunday & Thursday) for the following 10 weeks. Hence, some of the women only received tablets containing 10 µg 17β-estradiol and the remaining women only received tablets containing 25 µg 17β-estradiol. The estradiol profile when administering 25 or 10 µg 17β-estradiol was similar after the first dose (zero weeks of treatment) and after the above continuous treatment with 25 or 10 µg 17β-estradiol twice weekly for 10 weeks.

EXAMPLE 2

Treatment of atrophic vaginitis according to the present invention with low-dose 17β-estradiol tablets results in consistent, low absorption of estradiol without accumulation.

Objectives:

The vaginal absorption of 17β-estradiol (hereinafter designated E2) was evaluated and two low doses E2 (25 µg and 10 µg) were compared in postmenopausal women with atrophic vaginitis.

Design:

In a double-blind, randomized, parallel-group study, 58 postmenopausal women were treated with either 25 or 10 µg E2 for 12 weeks. Serum E2 and follicle stimulating hormone (hereinafter designated FSH) concentrations were measured throughout the study at specified intervals. The area under the curve, maximal concentration, and time to maximal concentration were determined for serum E2 concentrations. Maturation values of vaginal mucosal cells were assessed as an indicator of changes in the condition of the vaginal mucosa in response to treatment.

Results:

For both treatment groups, the E2 profiles were similar at weeks 0 and 12. The mean E2 concentrations, areas under the curve, and maximal concentrations were higher in the 25-µg E2 group than in the 10-µg E2 group. For the majority of patients in each treatment group, the areas under the curve remained below 600 pg·hr/mL at each time point, and the mean FSH concentrations were in the normal postmenopausal range. Patients in each treatment group showed significant improvement ($P \leq 0.01$) in the condition of the vaginal mucosa.

Conclusion:

Treatment with either 25- or 10-µg E2 vaginal tablets resulted in improvements in the vaginal mucosa and low absorption of estrogen without the systemic effects often associated with ERT. After 12 weeks of therapy for atrophic vaginitis, absorption patterns remained consistent, and patients did not experience an accumulation of circulating E2.

Studies have shown that vaginal ERT preparations can result in rapid and efficient absorption of E2 into systemic circulation. However, low-dose preparations that contain 10 and 25 μg E2 effectively relieve the symptoms of atrophic vaginitis without unwanted systemic side effects. A low-dose (25 μg) E2 vaginal tablet (Vagifem®; Novo Nordisk, Denmark) has been developed to treat estrogen deficiency-derived atrophic vaginitis. These vaginal tablets contain a film-coated hydrophilic cellulose matrix that adheres well to the vaginal mucosa and hydrates slowly to provide a controlled release of E2. They are designed to provide estrogenization of the vaginal mucosa while preventing significant increases in serum estrogen concentrations. In this study, the vaginal absorption of E2 was evaluated and two low doses of E2 (25 μg and 10 μg) were compared in postmenopausal women with atrophic vaginitis.

Materials and Methods

This single-center, randomized, double-blind, parallel-group study was conducted in Atlanta, Ga. The study was approved by the appropriate institutional review board, and written informed consent was obtained from each patient. The study was conducted in compliance with the Declaration of Helsinki of 1975, revised in 1983.

In this study, generally healthy, postmenopausal women (hysterectomized or nonhysterectomized), aged 45 years or older, were enrolled. Patients had no more than 5% superficial cells, as assessed by vaginal cytology evaluation, and serum E2 concentrations no greater than 20 pg/mL. Non-hysterectomized patients had endometrial thicknesses no greater than 4 mm, as determined by pelvic ultrasound. Patients with known or suspected history of breast cancer or other hormone-dependent tumors, acute thrombophlebitis or thromboembolic disorders associated with previous estrogen use, or vaginal infection requiring further treatment (at baseline) were excluded from the study, as were patients with genital bleeding of unknown etiology (within 12 months prior to screening). Patients were not to have used any type of vaginal, oral, or vulvar preparations within 7 days prior to screening; any exogenous corticosteroid or sex hormones within 8 weeks prior to baseline; any investigational new drug within the past 30 days; or diethylstilbestrol.

After the screening visit, patients received no study treatment during the 4-week run-in period prior to the baseline visit. At the baseline visit, patients were randomized to receive vaginal tablets containing either 25 or 10 μg E2 on a 1:1 basis using a computer-generated scheme. The vaginal tablets were identical in appearance. Patients inserted 1 tablet intravaginally, once daily for the initial 2 weeks of the study and then twice per week (Sunday and Thursday) for the remaining 10 weeks. Patients were instructed to use their medication at a consistent time each day, preferably in the morning. After the baseline visit, patients returned to the clinic at weeks 1, 2, 4, 8, and 12 for measurements of serum E2 and FSH, as well as assessments of vaginal cytology.

Upon presentation to the clinic for each visit, a vaginal cytology specimen was obtained. Patients then inserted the tablets. Blood samples were drawn 30 minutes before tablet insertion, and at 1, 2, 4, 5, 6, 7, 8, 10, 12, and 24 hours after insertion to determine the serum E2 concentration via radioimmunoassay. The blood samples obtained at 30 minutes before insertion, and at 6, 12, and 24 hours after insertion were also used to determine the FSH concentration via immunoradiometric assay.

The maturation value of vaginal mucosal cells was calculated from the percentages of parabasal, intermediate, and superficial cells according to the following equation:

maturation value=0×[parabasal cells, %]+0.5×[intermediate cells, %]+1.0×[superficial cells, %]

The pharmacokinetic parameters of area under the concentration-time curve from 30 minutes before tablet insertion to 24 hours after tablet insertion, maximal concentration, and time to maximal concentration were determined for serum concentrations of E2. Data for area under the curve and maximal concentration were converted to a logarithmic scale, and changes from first dose (at the baseline visit) in the logarithmic values were estimated using 95% confidence intervals derived from paired t-tests. Differences between treatment groups in the degree of absorption of E2 were determined using 95% confidence intervals derived from two sample t-tests based on the observed mean values of the logarithms of area under the curve and maximal concentration. Differences within treatment groups in FSH concentration were determined using the Wilcoxon signed rank test based on changes from baseline in mean concentrations at weeks 2 and 12. Mean concentrations were defined as the average concentrations obtained at 30 minutes before tablet insertion and 6, 12, and 24 hours after insertion. Baseline concentrations for E2 and FSH were defined as the values observed at 30 minutes before tablet insertion at the baseline visit.

This manuscript presents data for the evaluable patient population, which was defined as those patients who had serum E2 concentrations below 20 pg/mL at baseline and who had complete data available at the baseline visit and weeks 2 and 12.

Results

A total of 58 women were treated with vaginal tablets containing either 25 μg E2 (28 women) or 10 μg E2 (30 women). Ten women discontinued prematurely from the study. The evaluable patient population consisted of 42 women; 19 women received 25 μg E2, and 23 women received 10 μg E2. Demographic and baseline characteristics for the evaluable patient population are presented in Table 1. Patient characteristics were similar between treatment groups, with the exception of percentage of parabasal cells at baseline, which was significantly lower for patients in the 25-μg E2 group compared to those in the 10-μg E2 group (P=0.027, t-test).

Figure 1:
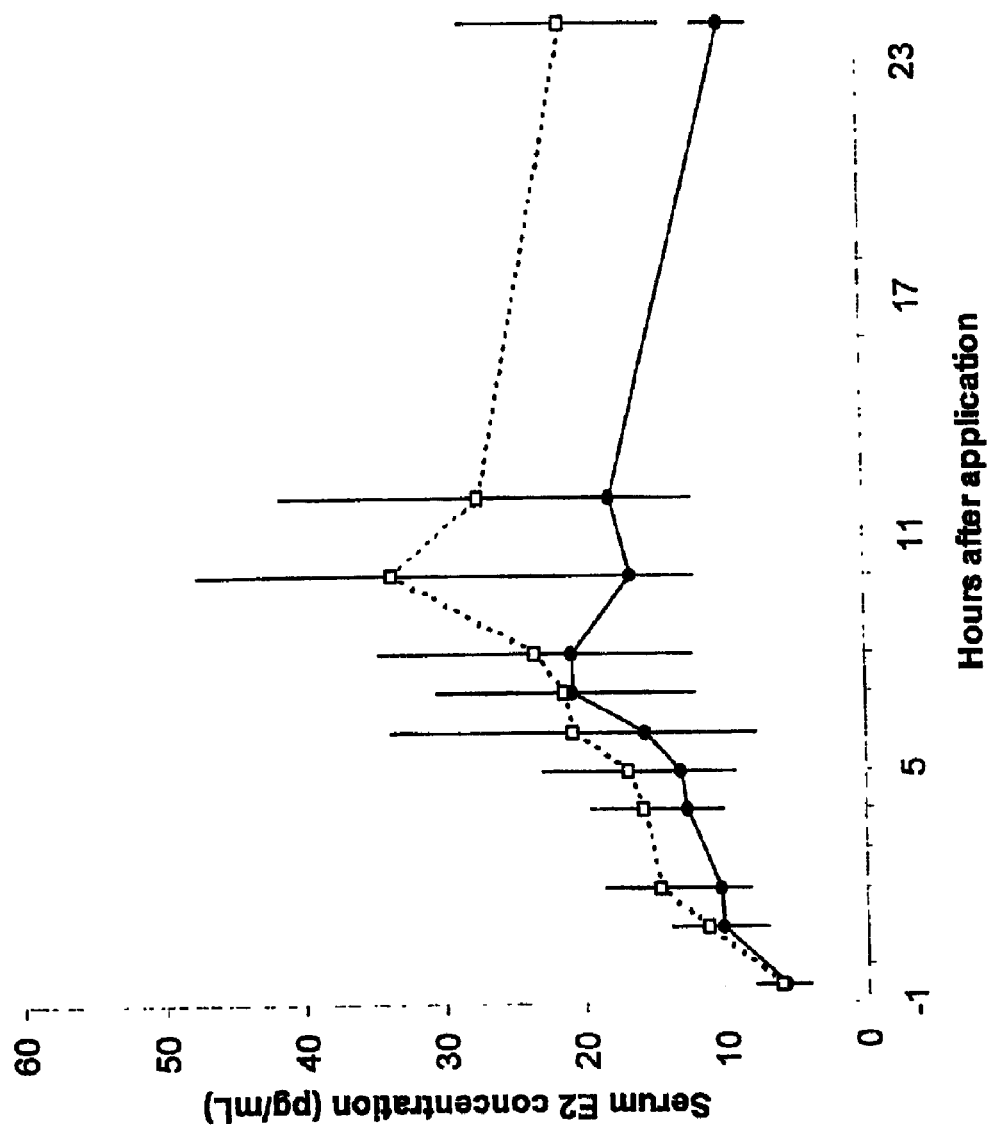
Figure 2:
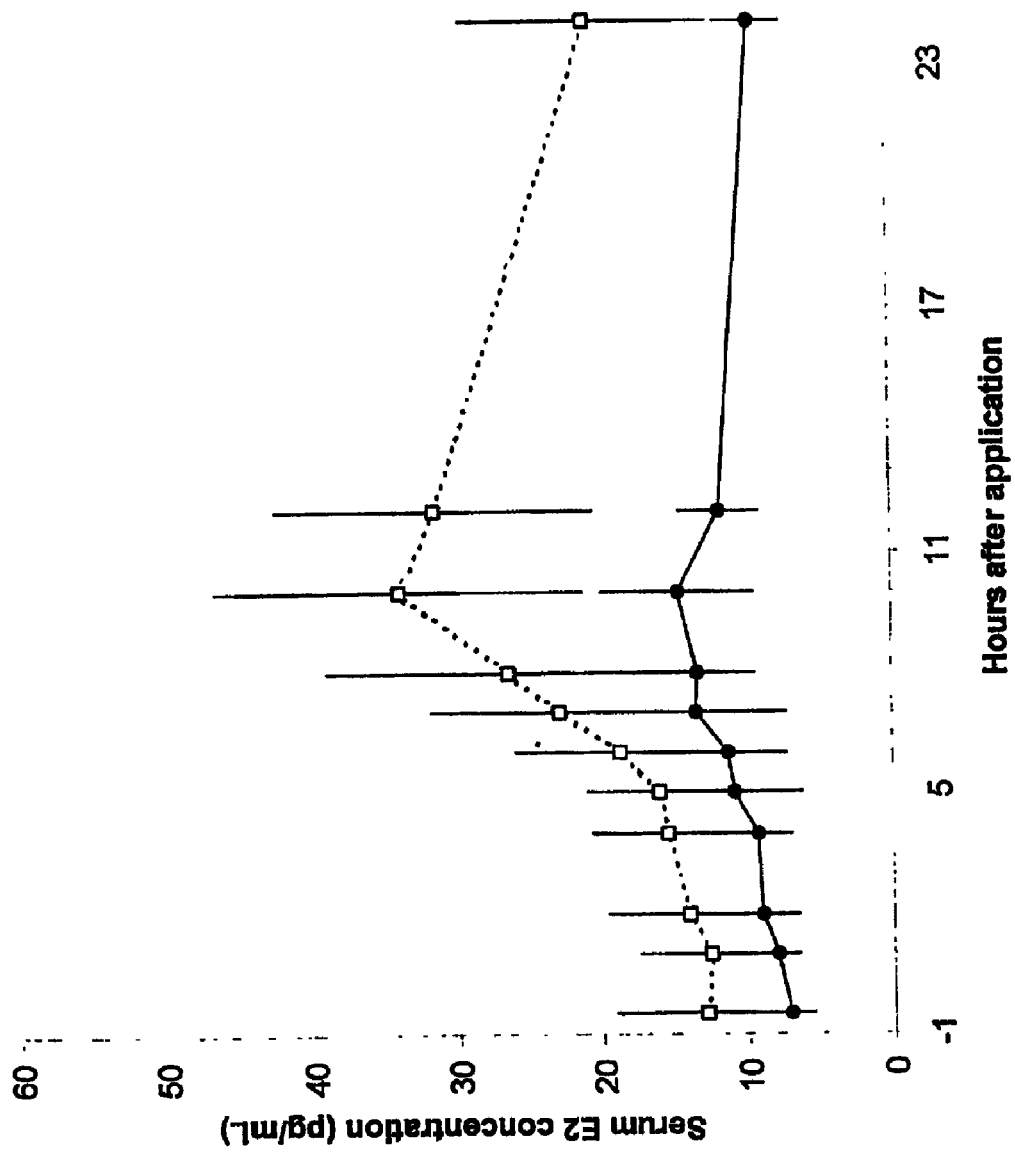

The 24-hour concentration profiles for serum E2 at weeks 0 and 12 are presented in FIGS. 1 and 2, respectively, and the associated pharmacokinetic characteristics are presented in Table 2. At weeks 0 and 12, the serum E2 profiles were similar within each treatment group. The serum E2 concentrations, as well as the corresponding mean area under the curve and maximal concentration, were higher for patients who received 25 μg E2 than for patients who received 10 μg E2. The average serum E2 concentrations over 24 hours were also higher in the 25-μg E2 group than in the 10-μg E2 group.

Figure 3:
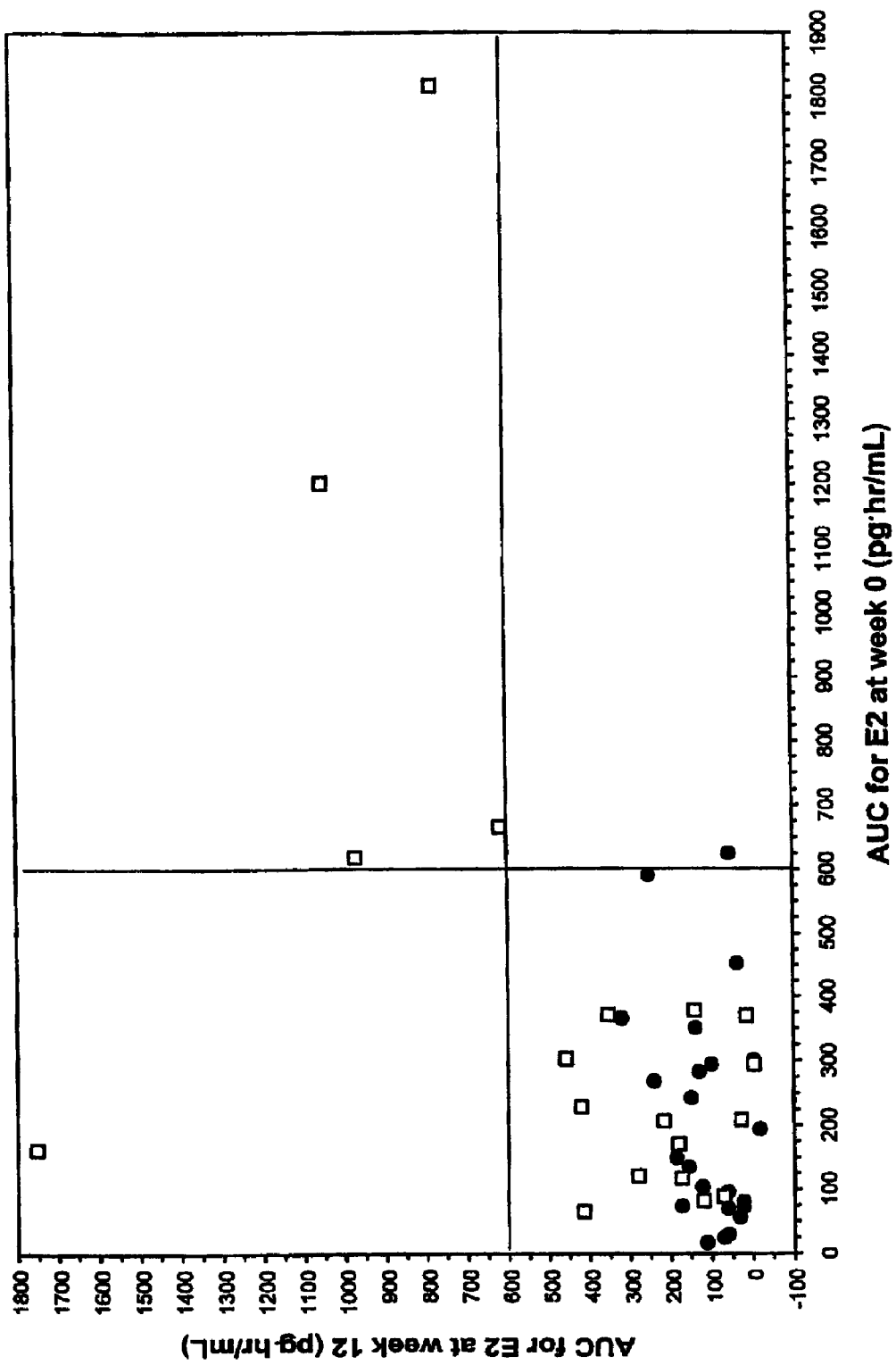

A comparison between the areas under the curve for serum E2 at weeks 0 and 12 is presented in FIG. 3. The majority of patients in each treatment group had areas under the curve below 600 pg·hr/mL at both time points (14 patients [74%] and 22 patients [96%] in the 25- and 10-μg E2 groups, respectively). A comparison between area under the curve for serum E2 and mean FSH concentration at week 12 is presented in FIG. 4. At week 12, the majority of patients in each treatment group had mean FSH concentrations in the normal postmenopausal range (at least 35 pg/mL); 3 patients in the 25-μg E2 group had mean FSH concentrations below 35 pg/mL.

The mean maturation value and mean change from baseline in maturation value are presented in Table 3. In each treatment group, patients experienced a significant increase in maturation value over baseline values (P≦0.001 at weeks 1 and 2, and P≦0.01 at week 12; 2-tailed, paired t-test). At all time points, mean maturation values and mean changes from base-line in maturation value were comparable between treatment groups. A comparison between the area under the curve for serum E2 and the maturation value at week 12 is presented in FIG. 5. The majority of patients in each treatment group (13 patients [68%] and 14 patients [64%] in the 25- and 10-μg E2 groups, respectively) showed increases in maturation values from the corresponding base-line values (53.4 and 51.0 in the 25- and 10-μg E2 groups, respectively).

Conclusions

The optimum intravaginal therapy will provide consistent estrogen absorption with adequate relief of vaginal symptoms without systemic absorption and the associated side effects. The low-dose vaginal tablets used in this study meet these criteria.

This study examined the systemic absorption of E2 in patients who received treatment with either 25- or 10-μg E2 vaginal tablets for 12 weeks. The majority of patients in each treatment group (74% in the 25-μg E2 group and 96% in the 10-μg E2 group) experienced low systemic absorption of E2 at both the beginning and end of the 12-week treatment period, as indicated by areas under the serum E2 concentration curve below 600 pg·hr/mL at each time point. Of the 6 remaining patients, 4 who did experience higher E2 absorption at week 12 also had areas under the curve greater than 600 pg·hr/mL at both week 0 and 12, suggesting that these patients were characteristically high E2 absorbers. It is likely that these patients would experience greater absorption of E2 as a result of any ERT.

The 24-hour serum E2 profiles at weeks 0 and 12 were similar for each treatment group, again indicating that overall, women had consistent E2 absorption patterns at the beginning and end of the treatment period. The average E2 concentrations at each time point were within the normal postmenopausal range (normal postmenopausal range for E2 concentration: $\leq 40$ pg/mL). The promising results from this study demonstrated consistent E2 absorption over 12 weeks of treatment.

In this study, after 12 weeks of treatment with either 25 or 10 μg E2, FSH concentrations were rarely suppressed to premenopausal levels, suggesting that the observed increase in serum E2 concentration is not associated with clinically significant systemic E2 potency. Both the 25- and 10-μg E2 dose levels demonstrated positive effects on an atrophic vaginal epithelium while maintaining low serum concentrations of E2. The improvement in vaginal health may be due to direct perfusion and/or lymphatic absorption of the local E2 through the vaginal epithelium. In this study, vaginal maturity was measured exclusively with the maturation value. Since the vaginal response is likely due to enhanced glycogenization and acidification of the vagina, monitoring the vaginal pH would provide another useful measure of vaginal health. Vaginal maturation with low concentrations of circulating E2 is a primary treatment goal of local vaginal ERT. Reduced risks of osteoporosis in postmenopausal women have also been observed. These benefits likely rely on the concentration of circulating E2 added to the endogenous production of E2 in bone, which is especially true in older, natural postmenopausal women. Since the average serum E2 concentrations were higher for patients who received 25 μg E2 than for those who received 10 μg E2, it is possible that patients who receive the lower dose may derive additional benefits because of very low likelihood of any systemic effect.

TABLE 1

Demographic and Baseline Characteristics (Evaluable Patients)

| | Treatment group | |
|---|---|---|
| Characteristic | 25 μg E2 (N = 19) | 10 μg E2 (N = 23) |
| Age (yr)[a] | 52.1 ± 5.6 (45–63) | 54.8 ± 5.1 (48–69) |
| Race | | |
| Caucasian | 16 (84.2%) | 18 (78.3%) |
| Other | 3 (15.8%) | 5 (21.7%) |
| Time since last menses (yr)[a] | 10.7 ± 7.6 (1–25) | 14.3 ± 8.7 (1–32) |
| Hysterectomized | | |
| Yes | 12 (63.2%) | 17 (73.9%) |
| No | 7 (36.8%) | 6 (26.1%) |
| E2 concentration at screening (pg/mL)[a] | 7.0 ± 2.8 (3–13) | 7.6 ± 3.7 (2–18) |
| Vaginal cytology at screening | | |
| Parabasal cells (%)[a] | 1.9 ± 2.5[b] (0–7) | 8.4 ± 12.9[b] (0–48) |
| Intermediate cells (%)[a] | 95.2 ± 7.8 (65–100) | 90.1 ± 12.4 (51–100) |
| Superficial cells (%)[a] | 2.9 ± 8.0 (0–35) | 1.5 ± 1.7 (0–6) |

SD = standard deviation; E2 = estradiol
[a]Data presented as mean ± SD (range).
[b]Statistically significant; P = .027 (t-test)

TABLE 2

Pharmacokinetic Parameters for 24-Hour Serum Estradiol Profiles (Evaluable Patients)

| | | Treatment group | |
|---|---|---|---|
| Time point | Pharmacokinetic characteristic | 25 μg E2 (N = 19) | 10 μg E2 (N = 23) |
| Week 0 | Area under the curve (pg · hr/mL)[a] | 538 ± 265 | 349 ± 107 |
| | Maximal concentration (pg/mL)[a] | 51 ± 34 | 35 ± 17 |
| | Time to maximal concentration (hr)[a] | 15 ± 9 | 9 ± 5 |
| | Serum concentration over 24 hours (pg/mL) | 22 | 15 |
| Week 12 | Area under the curve (pg · hr/mL)[a] | 563 ± 341 | 264 ± 120 |
| | Maximal concentration (pg/mL)[a] | 49 ± 27 | 22 ± 17 |
| | Time to maximal concentration (hr)[a] | 13 ± 6 | 10 ± 8 |
| | Serum concentration over 24 hours (pg/mL) | 23 | 11 |

E2 = estradiol; SD = standard deviation
[a]Data presented as mean ± SD.

TABLE 3

Mean Maturation Values and Changes From Baseline (All Patients)

| | Treatment group | | | |
|---|---|---|---|---|
| Time point | N | 25 μg E2 | N | 10 μg E2 |
| Week 0 | | | | |
| Mean ± SD | 25 | 52.4 ± 7.1 | 28 | 51.0 ± 6.2 |
| Week 12 | | | | |
| Mean ± SD | 20 | 58.4 ± 7.5 | 23 | 62.2 ± 15.7 |
| Mean change ± SD | 20 | 7.0 ± 8.7[b] | 23 | 11.2 ± 17.8[b] |

SD = standard deviation
[a]Statistically significant; P $\leq$ .001 (2-tailed, paired t-test)
[b]Statistically significant; P $\leq$ .01 (2-tailed, paired t-test)

EXAMPLE 3

Treatment according to the present invention with low-dose 17 β-estradiol tablets relieves vaginal symptoms, improves urogenital atrophy (vaginal health), and increases maturation of the vaginal and urethral epithelia (mucosa) without abnormal endometrial growth.

Objectives:

Vaginal tablets containing 25 or 10 µg 17 β-estradiol (herein designated E2) or placebo were evaluated and compared in postmenopausal women with atrophic vaginitis.

Methods:

In a multicenter, randomized, double-blind, placebo-controlled, parallel-group study, 230 postmenopausal women received treatment with 25 or 10 µg E2 or placebo for 12 weeks. Efficacy was measured with composite scores of vaginal symptoms (dryness, soreness, and irritation) and vaginal health (secretions, epithelial integrity, surface thickness, and pH). Vaginal and urethral cytology analyses were also performed, and the vaginal maturation value was determined. Safety assessments included endometrial biopsies.

Results:

Greater improvements in composite scores for vaginal symptoms and vaginal health characteristics were reported for patients in the active treatment groups than in the placebo group. Significantly greater improvements were reported at Weeks 7 and 12 ($P \leq 0.05$). At Week 12, over 75% of patients in the active treatment groups had vaginal pH values below 5.5 compared to approximately 40% of patients in the placebo group. Both vaginal and urethral cytology analyses indicated larger increases in percentages of superficial cells in the active treatment groups than in the placebo group. Correspondingly, increases in vaginal maturation value were higher in the active treatment groups than in the placebo group. One patient who received 25 µg E2 had an abnormal biopsy result.

Conclusions:

Both the 25- and 10-µg E2 vaginal tablets provided relief of vaginal symptoms, improved vaginal health, and increased maturation of both the vaginal and urethral mucosa without abnormal endometrial growth.

Introduction

As endogenous estrogen production declines during menopause, the vagina and other estrogen-dependent tissues gradually undergo atrophic changes. The loss of estrogen-influenced cellular maturation results in a condition identified as atrophic vaginitis. The symptoms of atrophic vaginitis include dryness, soreness, irritation, and dyspareunia. Additionally, the vaginal epithelium becomes more susceptible to infection and secondary inflammation.

Oral estrogen therapy has been associated with metabolic side effects as well as breast and endometrial hyperplasia.

Novo Nordisk has developed Vagifem™, a low-dose estrogen vaginal tablet that contains 25 fig E2 in a hydrophilic cellulose-based matrix. Pharmacokinetic studies of Vagifem™ have shown that in an atrophic vaginal epithelium, vaginally administered E2 is readily absorbed, but after normalization and maturation of the epithelium, E2 absorption is significantly reduced.

This study evaluated and compared the efficacy and safety of vaginal tablets containing 25 or 10 µg E2 or placebo during 12 weeks of therapy for vaginal atrophy.

Methods and Materials

This phase III, multicenter, randomized, double-blind, placebo-controlled, parallel-group study was conducted at 9 centers in the United States. The study was approved by the appropriate institutional review boards, and informed consent was obtained from each patient prior to beginning study procedures. The study was conducted in compliance with the Declaration of Helsinki of 1975, revised in 1983.

Women at least 45 years of age or older with moderate-to-severe vaginal dryness and soreness were enrolled. All patients were required to have serum E2 concentrations of 20 pg/mL or less and to have no more than 5% superficial vaginal cells. Patients with intact uteri were also required to be at least 12 months past natural menopause with an endometrial thickness of 5 mm or less.

Patients with creatinine levels greater than 1.4 mg/dL, bilirubin levels greater than 1.2 mg/dL, aspartate transaminase levels greater than 50 U/L, or hemoglobin levels less than 11.5 g/dL were excluded from the study. Patients with a known or suspected history of breast carcinoma, hormone-dependent tumor, genital bleeding of unknown etiology, acute thrombophlebitis or thromboembolic disorder associated with estrogen use, vaginal infection requiring treatment, allergy to the test drug or its constituents, or any serious disease or chronic condition that could interfere with study compliance were also excluded from the study. The use of an investigational drug within the 30 days preceding screening, any homeopathic preparation within the 7 days preceding study drug initiation, any exogenous corticosteroid or sex hormones within the 8 weeks preceding study drug initiation, or diethylstilbestrol was prohibited.

The purpose of this study was to compare 25 and 10 µg E2 and placebo. Using a computer-generated randomization scheme, subjects (patients) were randomized using a 2:2:1 ratio to receive vaginal tablets that contained 25 µg E2, 10 µg E2, or placebo. All vaginal tablets were identical in appearance. Patients inserted 1 tablet daily for 14 days. Thereafter, patients inserted 1 tablet twice per week (Sunday and Thursday) for the remainder of the trial. Patients were to insert the tablets at the same time each day (preferably at bedtime). Patients were evaluated for efficacy and safety at Week—4 (screening), Week 0 (baseline), and Weeks 2, 7, and 12.

Efficacy assessments included patient ratings of atrophic vaginitis symptoms, investigator ratings of vaginal health, and vaginal and urethral cytology. Patients used intensity ratings of none, mild, moderate, or severe to evaluate atrophic vaginitis symptoms (dryness, soreness, irritation, dyspareunia, and vaginal discharge). Intensity ratings were assigned ascending scores from 0 (none) to 3 (severe) for analysis. A composite score for atrophic vaginitis symptoms was defined as the average of the individual symptom scores for dryness, soreness, and irritation. This composite score did not include scores for dyspareunia (which was not evaluated by all patients) or vaginal discharge (which was rated as none or mild by the majority of patients). The composite score and the change from baseline for the composite score were examined at each time point. Differences within and between treatment groups were analyzed using an analysis of variance (ANOVA).

Investigators used a severity scale of none, mild, moderate, or severe to assess vaginal health characteristics (secretions, epithelial integrity, surface thickness, color, and pH). Severity categories were assigned ascending scores from 0 (none) to 3 (severe) for analysis. To avoid multiple endpoint issues, composite scores were defined. A composite score for vaginal health was defined as the average of the individual vaginal health characteristic scores. The composite score and the change from baseline for the composite score were examined at each time point. Differences within and between treatment groups were analyzed using an analysis of variance (ANOVA).

Vaginal and urethral cell samples were harvested and analyzed by independent cytologists to determine the percentages of parabasal, intermediate, and superficial cells. Maturation values were calculated according to the following equation:

maturation value=1.0×[superficial cells, %]+0.5×[intermediate cells, %]

Endometrial biopsies were performed at the end of the study in patients with intact uteri. The number of patients with abnormal biopsies was compared between treatment groups.

Results

A total of 91 women received 25 µg E2, 92 women received 10 µg E2, and 47 women received placebo. Demographic and baseline characteristics did not differ significantly between treatment groups, with the exception of race (Table 4). The percentage of nonwhite patients was significantly lower in the 25-µg E2 group than in the placebo group (P=0.026, Cochran-Mantel-Haenszel test). Nine patients (9.9%) in the 25-µg E2 group, 18 patients (19.6%) in the 10-µg E2 group, and 8 patients (17.0%) in the placebo group discontinued prematurely from the study.

Figure 6:
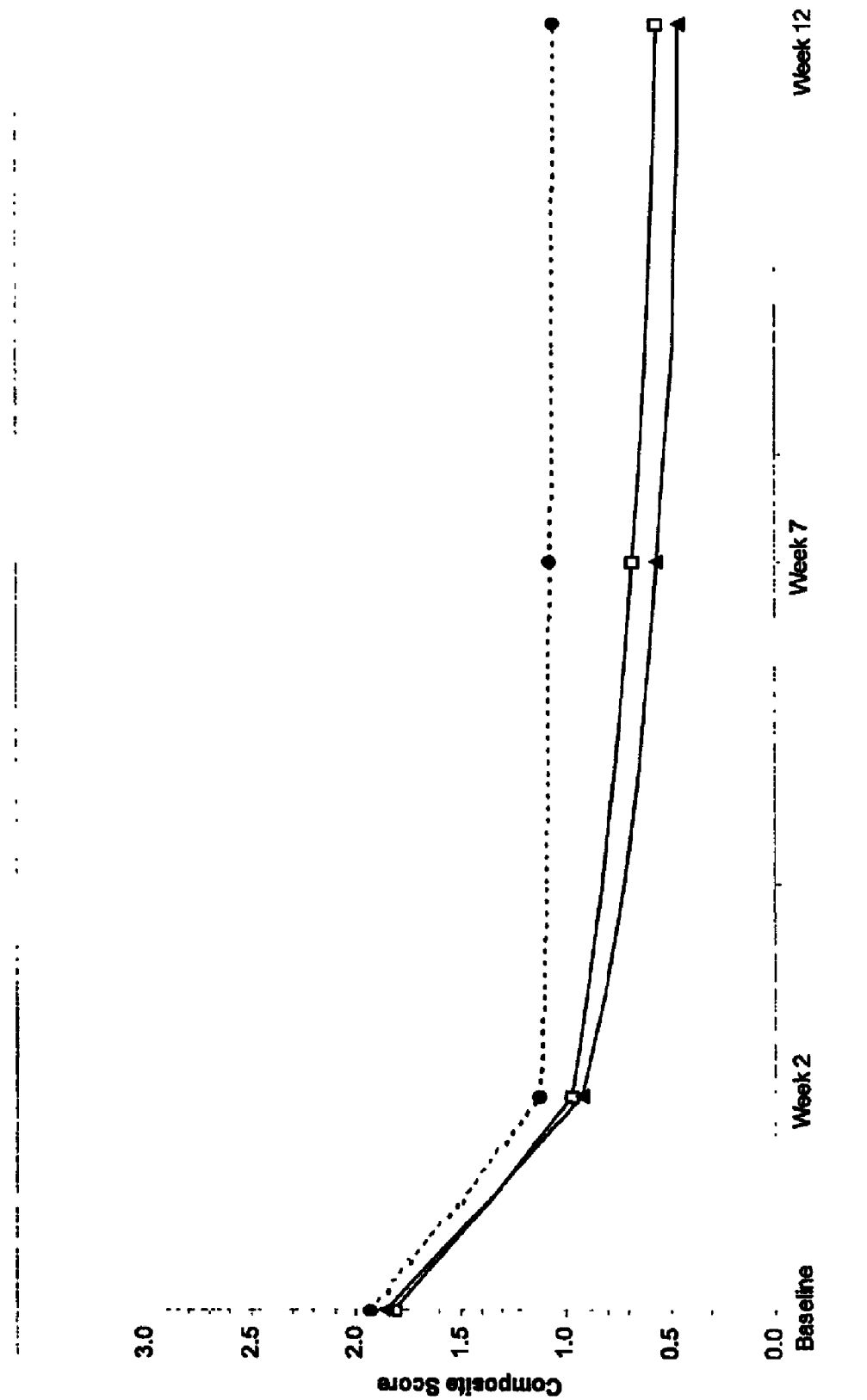

The vaginal symptom composite score profiles between Weeks 0 and 12 are presented in FIG. 6. At Week 0, the vaginal symptom composite scores measured approximately 1.9 in each treatment group. At Weeks 2, 7, and 12, vaginal symptom composite scores were significantly lower than the corresponding baseline values for each treatment group ($P \leq 0.001$; two-tailed paired t-test). In the active treatment groups (the 25- and 10-µg E2 groups), vaginal symptom composite scores continued to decrease after Week 0 and measured approximately 0.5 and 0.6 at Week 12, respectively. In contrast, in the placebo group, vaginal symptom scores remained nearly constant after Week 0 and measured approximately 1.1. At Weeks 7 and 12, the differences from baseline observed in the active treatment groups were significantly larger than those observed in the placebo group ($P \leq 0.01$ and $P \leq 0.05$ in the 25- and 10-µg E2 groups, respectively; two-tailed linear model analysis).

Figure 7:
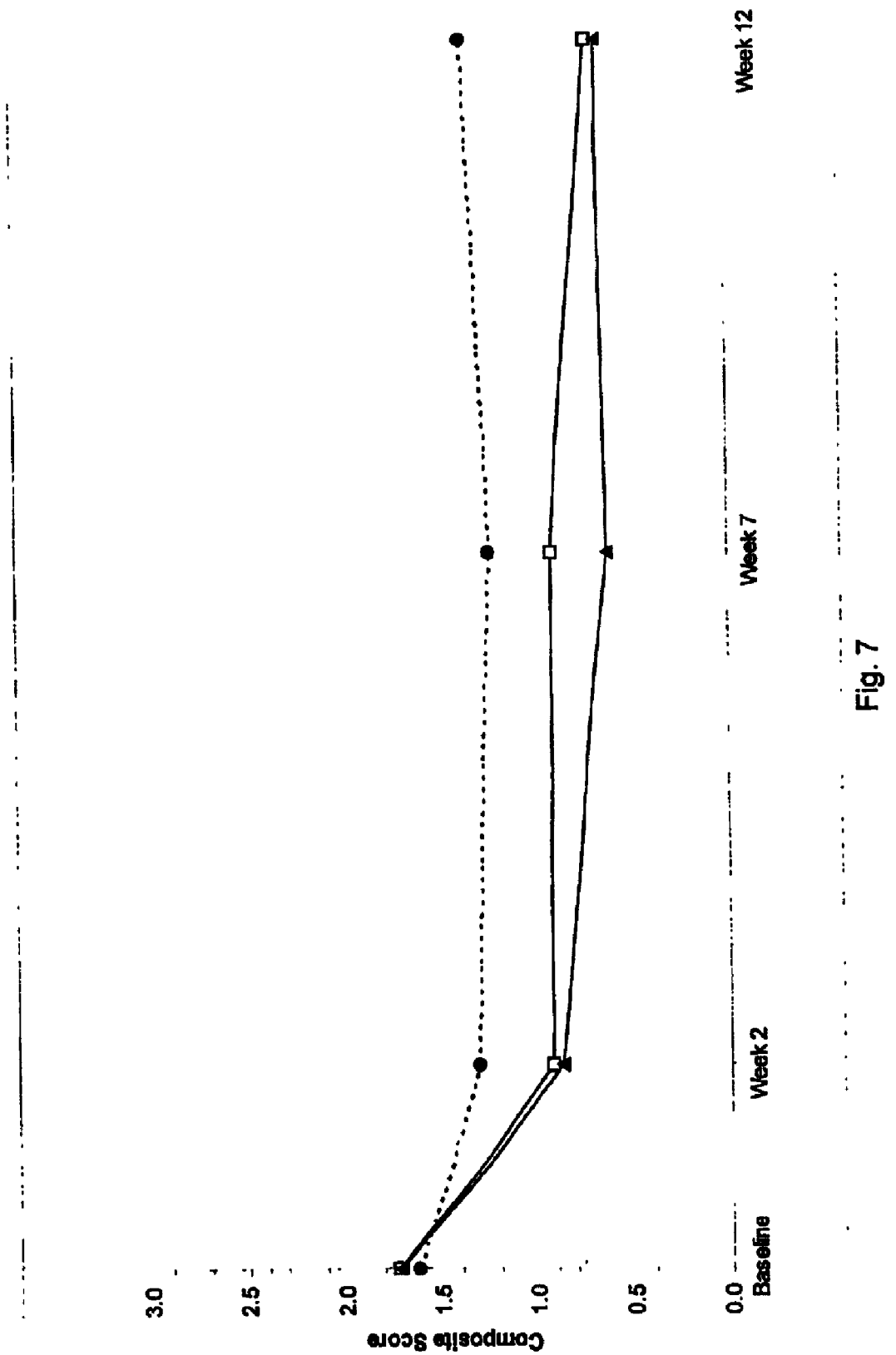

The urogenital (vaginal) health composite score profiles between Weeks 0 and 12 are presented in FIG. 7. At Week 0, the vaginal health composite scores measured approximately 1.7 in each treatment group. At Weeks 2, 7, and 12, vaginal health composite scores were significantly lower than the corresponding baseline values for each treatment group ($P \leq 0.01$; two-tailed paired t-test). At Weeks 2, 7, and 12, the decreases in vaginal health composite scores observed in the active treatment groups were significantly larger than those observed in the placebo group ($P \leq 0.001$; two-tailed linear model analysis). At Week 7, the decrease in vaginal health composite score was significantly larger in the 25-µg E2 group than in the 10-µg E2 (P=0.004, two-tailed linear model analysis).

The number and percentage of patients with vaginal pH values below 5.5 at Weeks 0, 2, 7, and 12 are presented in Table 5. At Week 0, approximately 35% of patients in each treatment group had vaginal pH values below 5.5. At Weeks 2, 7, and 12, the percentage of patients with vaginal pH values below 5.5 increased from the baseline percentages for each treatment group. These increases were significantly greater for patients in the active treatment groups than in the placebo group ($P \leq 0.05$; two-tailed linear model analysis). At Week 12, over 75% of patients in the active treatment groups and approximately 40% of patients in the placebo group had vaginal pH values below 5.5.

Figure 8:
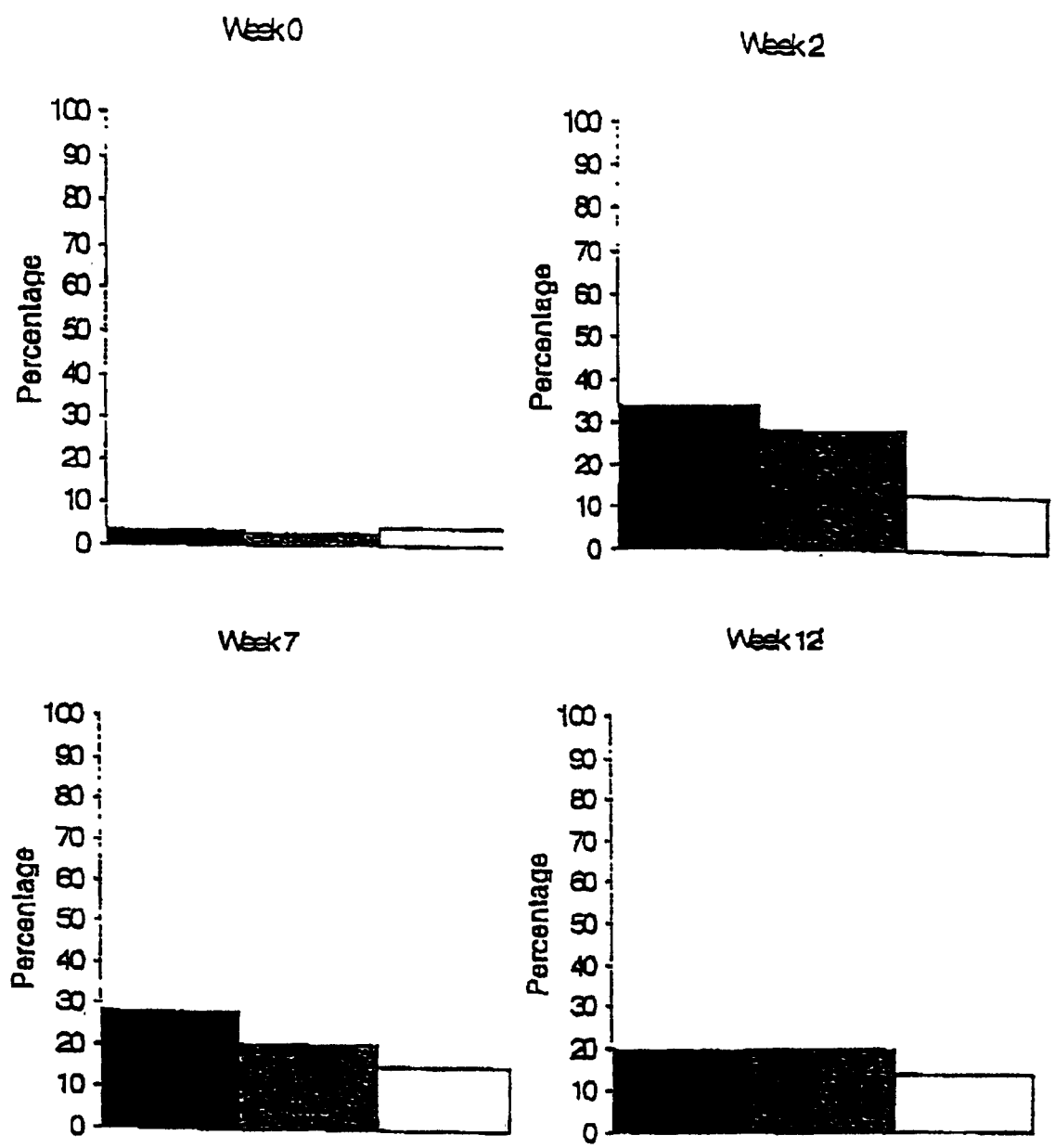

The percentage of superficial cells from vaginal cytology analysis at Weeks 0, 2, 7, and 12 are presented in FIG. 8. At all time points after Week 0, subjects in the active treatment groups showed either significant increases ($P \leq 0.05$) or trends toward increases in the percentage of superficial cells compared with subjects in the placebo group. These increases are presented in Table 7.

Figure 9:
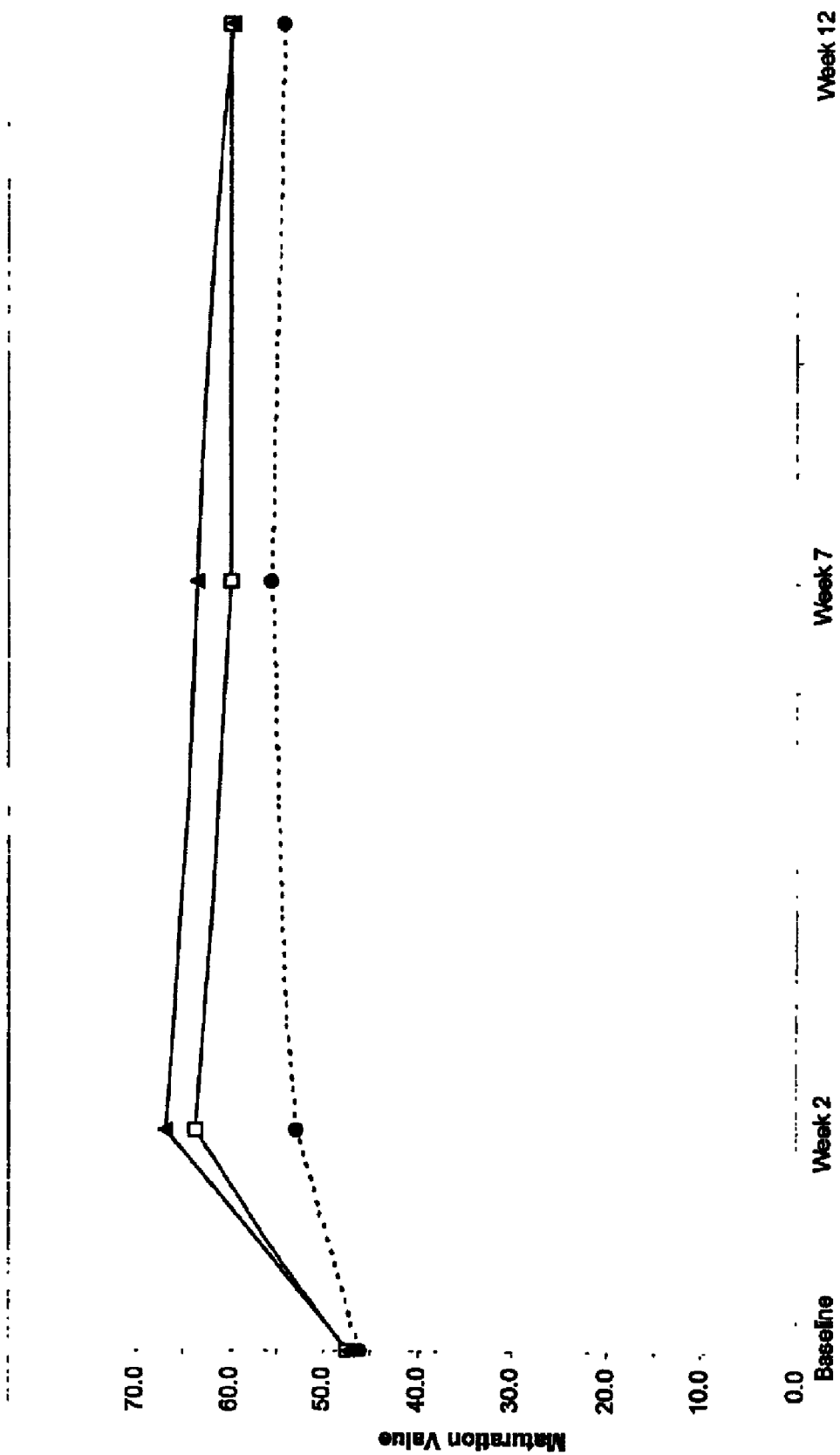

The maturation values at Weeks 0 through 12 are presented in FIG. 9. At Week 0, the maturation values measured approximately 45% in each treatment group. At each time point, the maturation values were significantly higher than the corresponding baseline values for each treatment group ($P \leq 0.01$; two-tailed paired t-test). The increases from baseline values were larger in the active treatment groups than in the placebo group. At Week 12, the maturation values measured approximately 60% in the active treatment groups and approximately 55% in the placebo group. At Weeks 2 and 7, the increases in maturation values observed in the 25-µg E2 group were significantly larger than those observed in the placebo group ($P \leq 0.05$; two-tailed linear model analysis). At Week 2, the increase in maturation value observed in the 10-µg E2 group was significantly larger than that observed in the placebo group (P=0.001; two-tailed linear model analysis).

Figure 10:
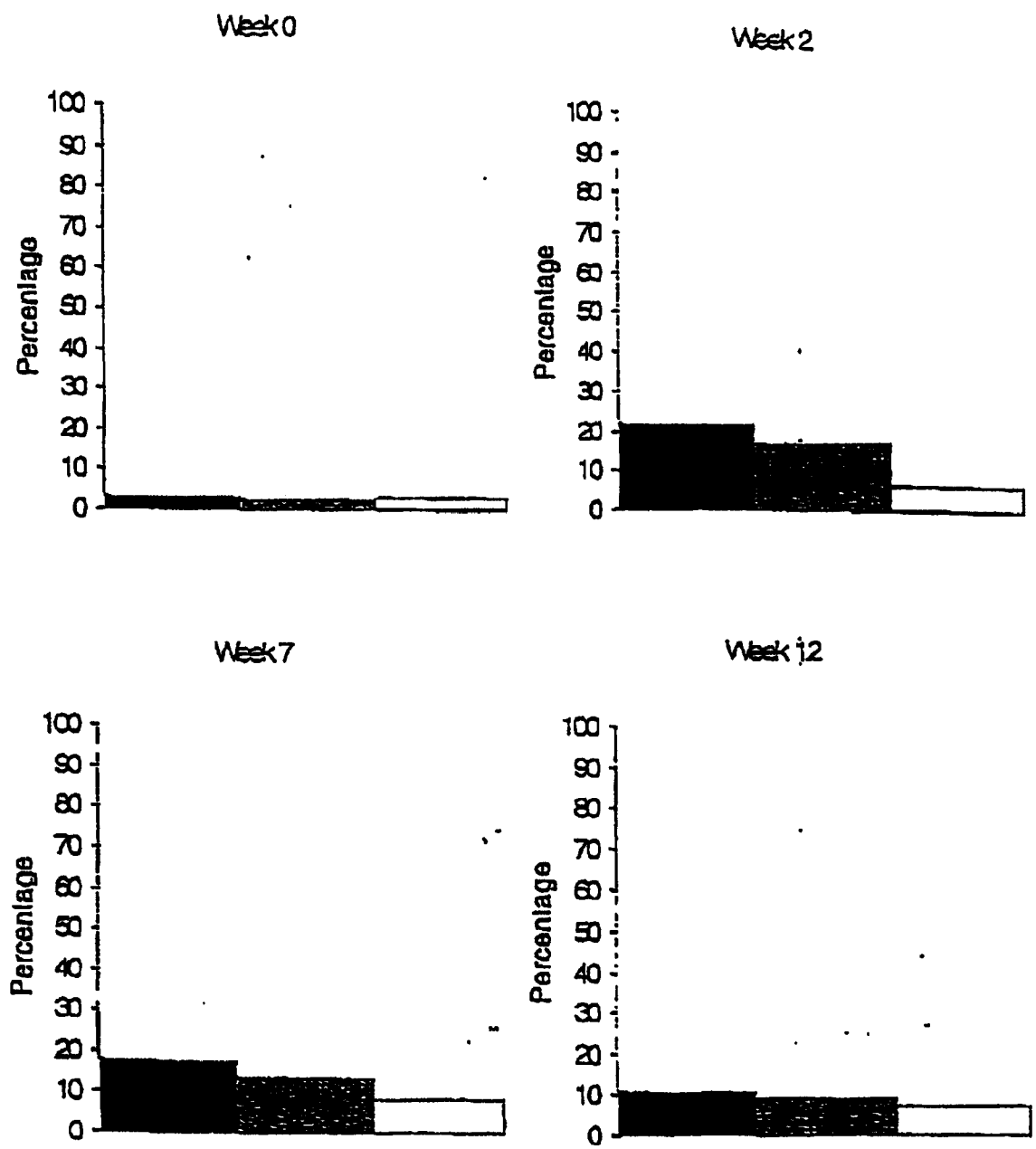

The percentage superficial cells from urethral cytology analysis at Weeks 0, 2, 7, and 12 are presented in FIG. 10. At all time points after Week 0, subjects in the active treatment groups showed either significant increases ($P \leq 0.05$) or trends toward increases in the percentage of superficial cells compared with subjects in the placebo group. These increases are presented in Table 8.

The percentage of superficial vaginal and urethral cells at Weeks 0 and 12 are presented in FIGS. 11 (a), (b), and (c) for the 25- and 10-µg E2 groups and the placebo group, respectively. At Week 0, the majority of the subjects in each treatment group had percentages of both superficial vaginal and urethral cells less that or equal to 5% (57 subjects [81%], 53 subjects [85%], and 34 subjects [97%] in the 25- and 10-µg E2 groups and the placebo group, respectively). At Week 12, more subjects in the active treatment groups that in the placebo group had increases in percentages of both superficial vaginal and urethral cells (52 subjects [74%], 44 subjects [71%], and 21 subjects [60%] in the 25- and 10-µg E2 groups and the placebo group, respectively).

The endometrial biopsy results at Week 12 are presented in Table 6. Of subjects with biopsies that yielded sufficient tissue, 1 subject in the 25-µg E2 group showed simple hyperplacia without atypia. However, there was no pretreatment biopsy for comparison.

The percentages of parabasal, intermediate, and superficial cells from vaginal cytology analysis at Weeks 0, 2, 7, and 12 are presented in FIG. 12. In most cases, the percentages of cells in each category changed significantly from the corresponding baseline values ($P \leq 0.01$; two-tailed paired t-test). At each time point, the percentage of superficial cells increased. At Weeks 2 and 7, the increases in percentage of superficial cells observed in the 25-µg E2 group were significantly larger than those observed in the placebo group ($P \leq 0.003$; two-tailed linear model analysis). At Weeks 2 and 12, the differences in percentage of superficial cells observed in the 10-µg E2 group were significantly larger than those observed in the placebo group ($P \leq 0.035$; two-tailed linear model analysis).

The percentages of parabasal, intermediate, and superficial cells from urethral cytology analysis at Weeks 0, 2, 7, and 12 are presented in FIG. 13. In most cases, the percentages of superficial and parabasal cells changed significantly from the corresponding baseline values (P≦0.05; two-tailed linear model analysis). Generally, the percentage of superficial cells increased, and the percentages of intermediate and parabasal cells decreased. At Weeks 2 and 7, the increases in percentage of superficial cells observed in the 25-μg E2 group were significantly larger than those observed in the placebo group (P≦0.044; two-tailed linear model analysis). At Week 2, the increases in percentage of superficial cells observed in the 10-μg E2 group were significantly larger than those observed in the placebo group (P≦0.018; two-tailed linear model analysis).

Conclusions

In this 12-week study, treatment with either 25- or 10-μg E2 tablets resulted in greater improvement in vaginal symptoms (as assessed by the patients) and vaginal health (as assessed by the investigators) than treatment with placebo. At each time point after baseline, improvements in the urogenital (vaginal) health composite scores were significantly greater in the active (25-μg and 10-μg E2) group than in the placebo group (P≦0.01). At each time point after 2 weeks of treatment, improvements in the vaginal symptom composite scores were also significantly greater (P≦0.05). Additionally subjects in the active treatment groups had statistically significant increases (P≦0.05) or trends toward increases in the percentage of superficial vaginal cells compared with subjects in the placebo group. In this study, treatment with 25- or 10-μg E2 resulted in comparable improvements as assessed by both patients and investigators.

Improvements in the symptoms of atrophic vaginitis become physically evident and manifest as changes in the vaginal mucosa. The condition of the vaginal mucosa can be determined through vaginal cytology measurements and maturation value. In this study, the percentages of immature parabasal and intermediate cells decreased, consequently increasing the percentages of more mature superficial cells in each treatment group. These changes are reflected in significant increases over baseline values in maturation value in each treatment group (P≦0.01). After 12 weeks of treatment, the maturation values for patients in the 25- or 10-μg E2 groups were approximately 60%, while the maturation values for patients in the placebo group were approximately 55%.

A second clinical measure of vaginal activity is the vaginal pH, a component of the urogenital (vaginal) health composite score. As estrogen production declines after menopause, lactobacilli, which produce lactic acid from vaginal glycogen, disappear from the vaginal flora and vaginal pH increases. Consequently, higher vaginal pH values are associated with a lack of estrogen in the vaginal mucosa. In this study approximately twice as many patients who received 25 or 10 μg E2 than those who received placebo had vaginal pH values below 5.5 after 12 weeks of treatment (75% versus 40%, respectively). The results from analysis of vaginal cytology and pH indicate a positive effect of the 25- and 10-μg E2 vaginal tablets on estrogenation of the vaginal epithelum (mucosa).

The lower portions of the vaginal and urinary tracts have the same embryological origin, and genital tract disorders such as atrophic vaginitis are often accompanied by atrophic changes in the urinary tract that may include dysuria, stress incontinence, and urinary tract infections. Consequently, estrogen therapy may also have an effect on the urethral epithelium. In this study, the condition of the urethral epithelium was determined through urethral cytology. Similar to the vaginal cytology analysis, the percentages of parabasal cells in the urethral epithelium decreased and the percentage of superficial cells increased for each treatment group. Although this study was not designed to further determine benefits to the urinary tract, this urethral maturation could be attributed to estrogenation of the urethral mucosa.

Thus, although the 25-μg E2 vaginal tablets used in this study appear to positively affect the vaginal and urethral epithelia, they were not associated with endometrial abnormalities.

TABLE 4

Demographic and Baseline Characteristics

| Characteristic | Treatment group | | |
|---|---|---|---|
| | 25 μg E2 (N = 91) | 10 μg E2 (N = 92) | Placebo (N = 47) |
| Age (yr)[a] | 58.3 ±7.4 (46–78) | 57.7 ± 6.5 (46–79) | 57.6 ± 4.8 (50–70) |
| Race | | | |
| White | 88 (96.7%) | 83 (90.2%) | 41 (87.2%) |
| Non-white | 3 (3.3%)[b] | 9 (9.8%) | 6 (12.8%)[b] |
| Time since last menses (yr)[a] | 14.8 ±9.6 (1–40) | 13.5 ± 7.8 (1–34) | 13.6 ± 8.1 (1–33) |
| Hysterectomized | | | |
| Yes | 42 (46.2%) | 44 (47.8%) | 23 (48.9%) |
| No | 49 (53.8%) | 48 (52.2%) | 24 (51.1%) |

SD = standard deviation
[a]Mean ± SD (range)
[b]Statistically significant; P = .026 (Cochran-Mantel-Haenszel test)

TABLE 5

Number and Percentage of Patients With Vaginal pH Values Below 5.5

| | Treatment group | | |
|---|---|---|---|
| Time point | 25 μg E2 n/N (%) | 10 μg E2 n/N (%) | Placebo n/N (%) |
| Week 0 | 31/90 (34.4) | 27/89 (30.3) | 17/46 (37.0) |
| Week 2 | 64/87 (73.6)[a] | 67/84 (79.8)[b] | 21/43 (48.8) |
| Week 7 | 71/83 (85.5)[b,d] | 57/80 (71.3)[c] | 23/44 (52.3) |
| Week 12 | 63/79 (79.7)[b] | 54/71 (76.1)[b] | 15/38 (39.5) |

A two-tailed linear model analysis was used to compare treatment groups at each time point.
[a]Comparison with placebo, statistically significant; P ≦ .01
[b]Comparison with placebo, statistically significant; P ≦ .001
[c]Comparison with placebo, statistically significant; P ≦ .05
[d]Comparison with 10 μg 17 β-E2, statistically significant; P ≦ .05

TABLE 6

Endometrial Biopsy Results at Week 12

| | Treatment group | | |
|---|---|---|---|
| Result | 25 μg E2 (N = 32) | 10 μg E2 (N = 32) | Placebo (N = 21) |
| Normal[a] | 28 (87.5%) | 25 (78.1%) | 18 (85.7%) |
| Abnormal[b] | 1 (3.1%) | 0 (0.0%) | 0 (0.0%) |
| Other[c] | 3 (9.4%) | 7 (21.9%) | 3 (14.3%) |

[a]Results indicative of an atrophic endometrium, weakly proliferative endometrium, proliferative endometrium, or secretory endometrium were classified as normal.
[b]Results indicative of endometrial hyperplasia (simplex, complex, or atypical) or carcinoma were classified as abnormal.
[c]Results indicative of a menstrual endometrium, mucosal polyps, insufficient tissue, or other finding were classified as other.

TABLE 7

Mean and mean change from baseline in percentage of superficial vaginal cells

| | Treatment Group | | | | | | | |
|---|---|---|---|---|---|---|---|---|
| Time | 25 μg E2 | | | 10 μg E2 | | | Placebo | |
| Point | N | Mean | Change | N | Mean | Change | N | Mean | Change |
| Week 0 | 86 | 4.0 | | 79 | 3.1 | | 45 | 4.3 | |
| Week 2 | 85 | 34.2 | 30.7[a] | 76 | 28.3 | 25.0[a] | 42 | 13.1 | 8.6 |
| Week 7 | 80 | 28.2 | 23.9[b,c] | 72 | 20.4 | 17.1 | 41 | 15.1 | 10.4 |
| Week 12 | 75 | 19.9 | 15.4 | 68 | 20.1 | 16.9[d] | 36 | 13.8 | 9.0 |

A two-tailed linear model analysis was used to compare treatment groups at each time point.
[a]Comparison with placebo, statistically significant; P ≤ .001
[b]Comparison with placebo, statistically significant; P ≤ .01
[c]Comparison with 10 μg E2, statistically significant; P ≤ .05
[d]Comparison with placebo, statistically significant; P ≤ .05

TABLE 8

Mean and mean change from baseline in percentage of superficial urethral cells

| | Treatment Group | | | | | | | |
|---|---|---|---|---|---|---|---|---|
| Time | 25 μg E2 | | | 10 μg E2 | | | Placebo | |
| Point | N | Mean | Change | N | Mean | Change | N | Mean | Change |
| Week 0 | 86 | 3.2 | | 83 | 2.5 | | 42 | 3.0 | |
| Week 2 | 83 | 21.9 | 19.2[a,b] | 79 | 16.7 | 14.1[c] | 34 | 6.5 | 3.3 |
| Week 7 | 77 | 17.6 | 14.2[d] | 70 | 13.5 | 10.7 | 38 | 8.6 | 5.5 |
| Week 12 | 70 | 11.2 | 7.5 | 64 | 9.5 | 6.8 | 34 | 7.0 | 3.6 |

A two-tailed linear model analysis was used to compare treatment groups at each time point.
[a]Comparison with placebo, statistically significant; P ≤ .001
[b]Comparison with 10 μg E2, statistically significant; P ≤ .05
[c]Comparison with placebo, statistically significant; P ≤ .01
[d]Comparison with placebo, statistically significant; P ≤ .05

EXAMPLE 4
Manufacture of 10 μg Tablets
Suspension of Estradiol 10.3 g estradiol hemihydrate (equivalent to 10.0 g estradiol, anhydrous) is suspended in a solution of hypromellose (14.8 g) in purified water 15.6 L) while stirring.

Granulation

Blending, granulation, and drying are performed in a fluid bed.

Hypromellose (53.69 kg), lactose monohydrate (17.90 kg), and maize starch (8.00 kg) are sucked into the fluid bed through a sieve and then blended.

The granulation takes place by spraying the suspension of estradiol on the mixture of excipients. After spraying the granulate is dried.

Blending

Sieving is performed and magnesium stearate (400 g) is blended into the granulate Compression The tablets are compressed using a rotary tablet press.

Preparation of Film-coating Solution

Hypromellose (400 g) and macrogol 6000 (50 g) are dissolved in purified water (9.55 kg)

Film-coating

In a coating pan, the tablets are coated with the coating solution (0.576 mg dried substance/tablet), using an air atomizing spray system. After coating sampling of tablets to release testing takes place.

EXPLANATION TO THE FIGURES

FIG. 1. Serum concentrations of estradiol at week 0.

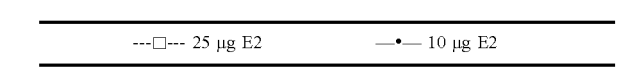

FIG. 2. Serum concentrations of estradiol at week 12.

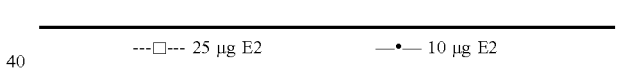

FIG. 3. Area under the serum estradiol curve at weeks 0 and 12.

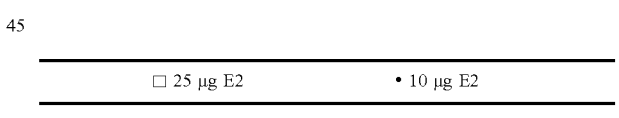

Figure 4:
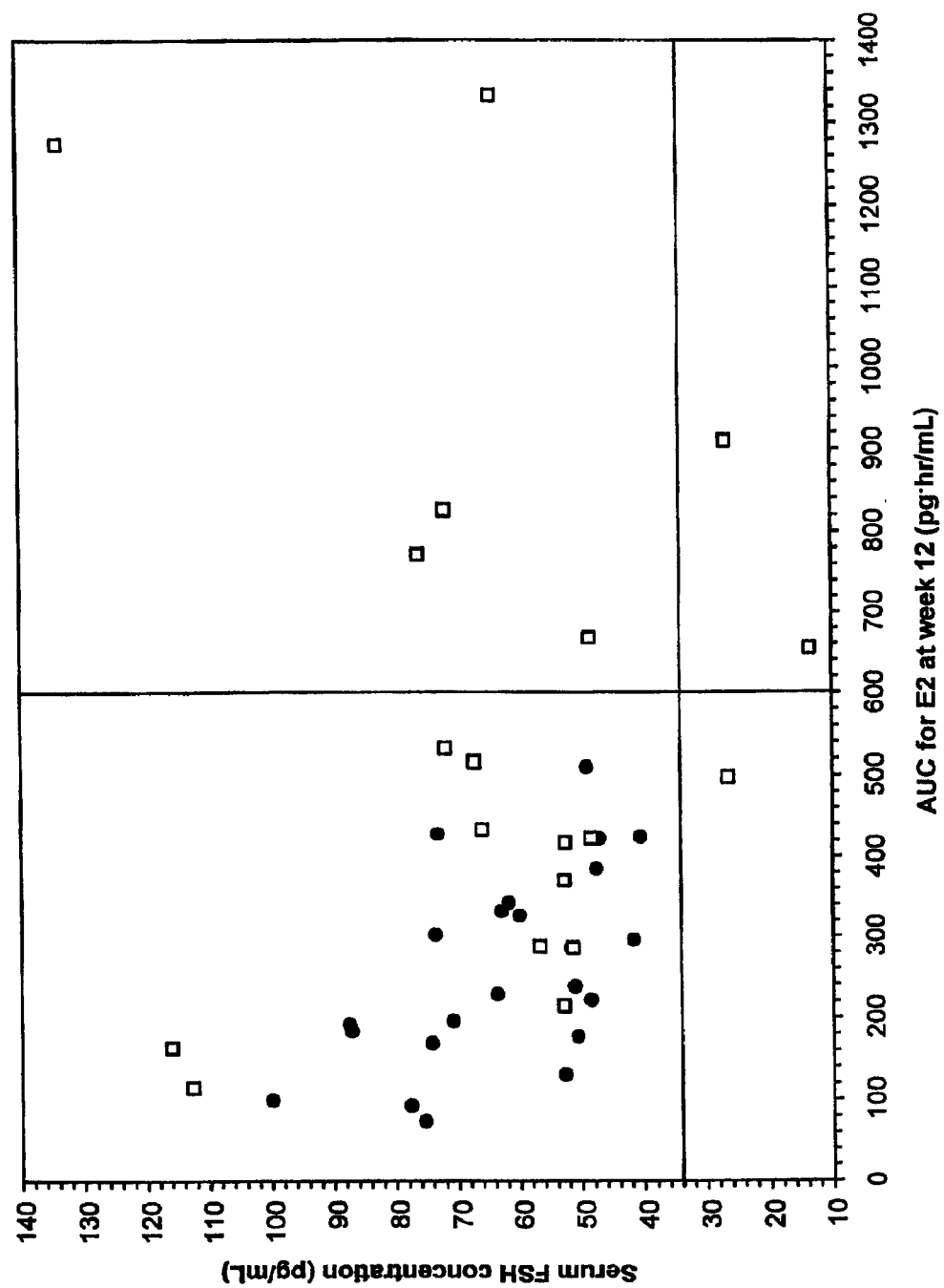

FIG. 4. Area under the serum estradiol curve and serum FSH concentration at week 12.

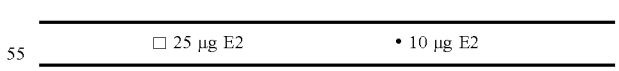

Figure 5:
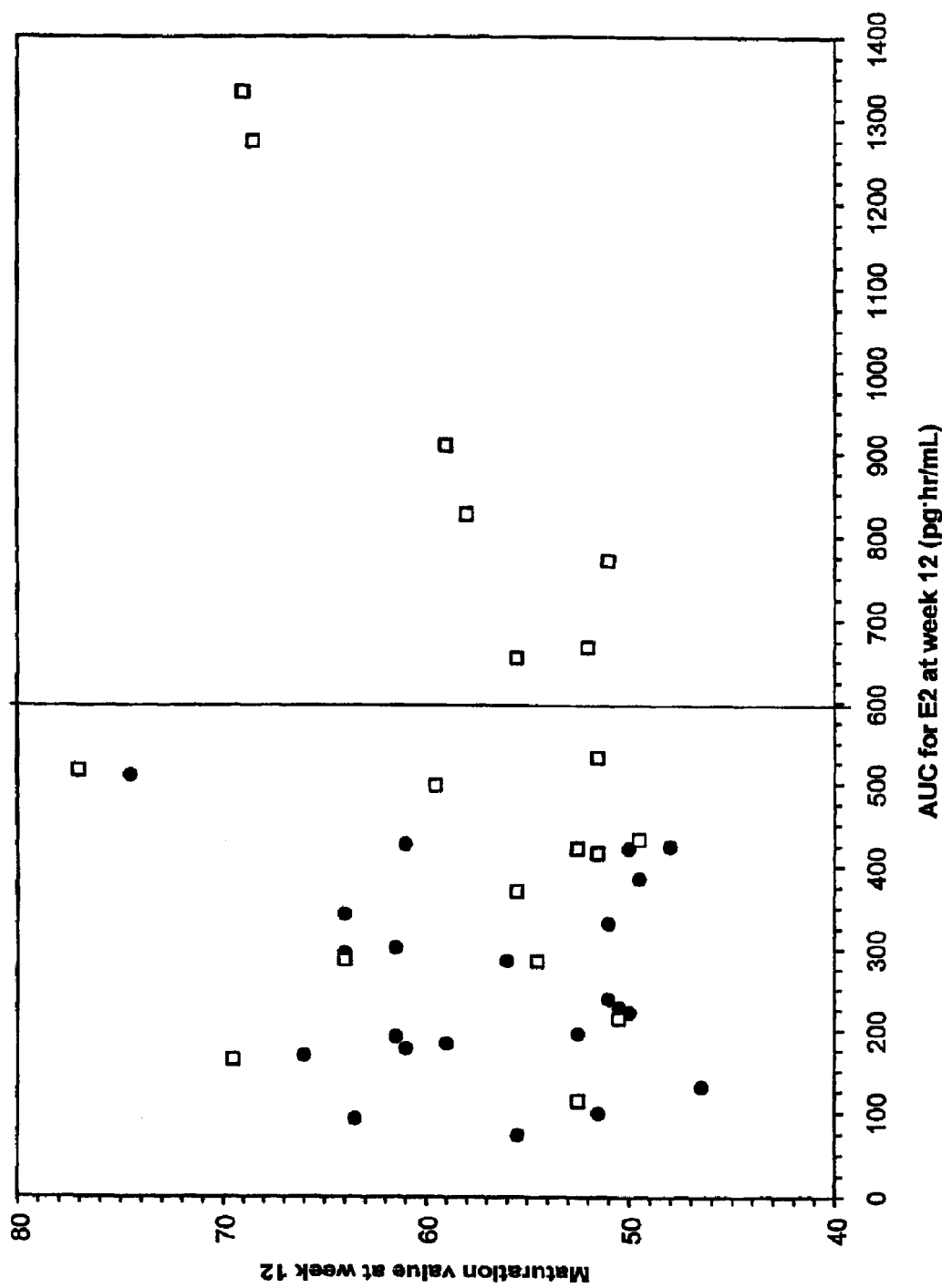

FIG. 5. Area under the serum estradiol curve and maturation value at week 12. Maturation values at baseline were 52.4 in the 25-μg E2 group and 51.0 in the 10-μg E2 group.

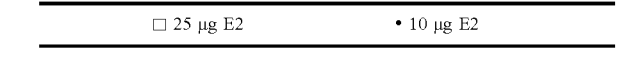

FIG. 6. Vaginal symptom composite score profiles—subjects who received at least 1 dose of study medication, had baseline assessment, and had at least 1 post-baseline assessment

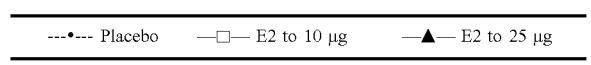

FIG. 7. Vaginal health composite score profiles—subjects who received at least 1 dose of study medication, had baseline assessment, and had at least 1 post-baseline assessment

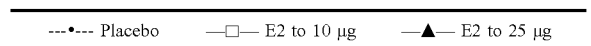

FIG. 8. Vaginal cytology results (percentage of superficial cells)—subjects who received at least 1 dose of study medication, had baseline assessment, and had at least 1 post-baseline assessment.

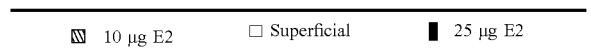

FIG. 9. Maturation values—subjects who received at least 1 dose of study medication, had baseline assessment, and had at least 1 post-baseline assessment

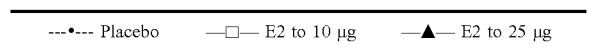

FIG. 10. Urethral cytology results—subjects who received at least 1 dose of study medication, had baseline assessment, and had at least 1 post-baseline assessment

FIG. 11. Percentages of superficial vaginal and urethral cells—subjects who had superficial vaginal and urethral cell assessments at Weeks 0 and 12

(a) 25 µg E2
(b) 10 µg E2
(c) Placebo

FIG. 12. Vaginal cytology results

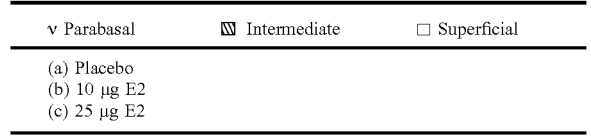

(a) Placebo
(b) 10 µg E2
(c) 25 µg E2

FIG. 13. Urethral cytology results

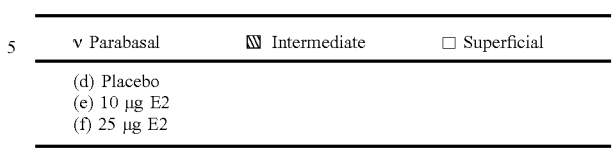

(d) Placebo
(e) 10 µg E2
(f) 25 µg E2

What is claimed is:

1. A method for treating atrophic vaginitis in a patient in need of such treatment, said method comprising administering vaginally to said patient an amount of about 10 µg estradiol, wherein administration of said amount occurs once or twice per week and wherein said estradiol is administered in tablet form.

2. A method according to claim 1, wherein the patient is a menopausal or post-menopausal woman.

3. A method for treating atrophic vaginitis in a patient in need of such treatment, said method comprising administering vaginally to said patient an amount of about 5 µg estradiol, wherein administration of said amount occurs twice weekly and wherein said estradiol is administered in tablet form.

4. A method according to claim 1, wherein no progestogen is administered.

5. A method according to claim 1, wherein said at least once-weekly administration occurs over a period of time of more than 2 weeks.

6. A method according to claim 5, wherein said period of time is more than 1 month.

7. A method according to claim 6, wherein said period of time is more than 3 months.

8. A method according to claim 1, wherein each tablet comprises, in addition to estradiol or a therapeutically equivalent amount of a salt thereof, about 53.7 mg hypromellose, about 17.9 mg lactose monohydrate, about 8 mg maize starch, about 0.4 mg magnesium stearate.

9. A method according to claim 1, wherein each tablet is coated with a film consisting of about 0.5 mg hypromellose and about 0.06 mg macrogel 6000 (polyethylene glycol 6000 NF).

10. A method according to claim 1, wherein there is undetectable systemic absorption of said estradiol following said administration.

11. A method according to claim 1, wherein said treatment results in a vaginal pH value below bout 5.5.

12. A method according to claim 1, wherein said treatment results in one or more of: Relief of vaginal symptoms, improved urogenital atrophy, decreased vaginal pH, and improved cytologic maturation of the vaginal and/or urethral mucosa.

* * * * *